United States Patent [19]

Yamamoto et al.

[11] Patent Number: 5,670,315
[45] Date of Patent: Sep. 23, 1997

[54] NUCLEIC ACID DETERMINATION EMPLOYING PYRYILIUM DYE

[75] Inventors: Nobuko Yamamoto, Isehara; Tadashi Okamoto, Yokohama; Yoshinori Tomida, Atsugi; Tetsuya Yano, Isehara; Takeshi Miyazaki, Ebina; Masahiro Kawaguchi, Atsugi, all of Japan

[73] Assignee: Canon Kabushiki Kaisha, Tokyo, Japan

[21] Appl. No.: 263,072

[22] Filed: Jun. 21, 1994

[30] Foreign Application Priority Data

Sep. 13, 1993 [JP] Japan .................. 5-227204
Feb. 21, 1994 [JP] Japan .................. 6-022895

[51] Int. Cl.$^6$ .................. C12Q 1/68; C12P 19/34
[52] U.S. Cl. .................. 435/6; 435/91.2; 435/288.2; 435/288.4; 435/288.5
[58] Field of Search .................. 435/6, 91.2, 810, 435/287, 288.3, 288.4, 288.5, 288.1, 288.2

[56] References Cited

U.S. PATENT DOCUMENTS

| | | | |
|---|---|---|---|
| 4,555,396 | 11/1985 | Frank et al. | 424/3 |
| 4,840,784 | 6/1989 | Frank et al. | 424/3 |
| 5,229,297 | 7/1993 | Schnipelsky et al. | 436/94 |

FOREIGN PATENT DOCUMENTS

| | | |
|---|---|---|
| 0232967 | 3/1986 | European Pat. Off. |
| 0229943 | 7/1987 | European Pat. Off. |
| 0320308 | 6/1989 | European Pat. Off. |
| 0439036 | 7/1991 | European Pat. Off. |
| 0455517 | 11/1991 | European Pat. Off. |
| 0487218 | 5/1992 | European Pat. Off. |
| 0512334 | 11/1992 | European Pat. Off. |
| 5-237000 | 9/1993 | Japan . |
| WO86-03227 | 6/1986 | WIPO . |
| WO89-10415 | 11/1989 | WIPO . |

OTHER PUBLICATIONS

Yamamoto et al., *Nucl. Acids Res* 23(8), 1445–1446 (1995).
Picard et al., *Appl. Environ. Microbiol.* 58(9), 2717–2722 (1992).
Yamamoto et al., *Nucl. Acids Symp. Ser.* 29, 83–84 (1993).
Morrison et al. "Solution–Phase Detection . . . Hybridization", Anal. Biochem., vol. 183, No. 2, pp. 231–244 (1989).
Strobel et al., "Preparation and Characterization . . . DNA Hybridization", Bioconjugate Chem., vol. 2, pp. 89–95 (1991).
Rahman et al., "Complexes involving . . . (Cv (II)", Carcinogenesis, vol. 11, No. 11, pp. 2001–2003 (1990).
Cardullo et al., "Detection of Nucleic Acid . . . Transfer", Proc. Nalt. Acad. Sci. USA, vol. 85, pp. 8790–8794 (1988).
Puruggan et al., "Accelerated Electron . . . by DNA", Science, vol. 241, No. 23, pp. 1645–1649 (1988).
Murphy et al., "Long–Range Photoinduced . . . DNA Helix", Science, vol. 262, No. 12, pp. 1625–1629 (1993).
Cullis et al., "Electron Conduction and Trapping in DNA", J. Chem. Soc. Faraday Trans., vol. 86, No. 3, pp. 591–592 (1990).
Detty, "Rational design . . . chacogenapyrlium dyes", Proc. SPIE, vol. 847, New Directions in Photodynamic Therapy, pp. 68–73 (1987).
Fromherz et al., "Photoinduced Electron . . . Methylbiologen", J. Am. Chem. Soc., vol. 108, pp. 5361–5362 (1986).
Barton et al., "DNA–Mediated Photoelectron Transfer Reactions", J. Am. Chem. Soc., vol. 108, pp. 6391–6393 (1986).
Brun et al., "Dynamics of Electron . . . Bases", J. Am. Chem. Soc., vol. 114, pp. 3656–3660 (1992).
Latt et al., "New Fluorochromes, Compatible With High Wavelength Excitation, for Flow Cytometric Analysis of Cellular Nucleic Acids", Cytometry, vol. 5, No. 4, Jul., 1984, New York, pp. 339–347.
D. Basting et al., "New Laser Dyes", Applied Physics, vol. 3, 1974, pp. 81–88.
G. Haucke et al., "Absorption And Fluorescence of Pyrylium Salts", Ber. Bunsenges. Phys. Chem., vol. 96, No. 7, 1992, pp. 880–886.
Halvorson, et al. "Means of Determining Bacterial Population by the Dilution Method", J. Bact., vol. 25, pp. 101–121 (1933).
Wisinger, et al. "About Thiopyrylcyanine", Helv. Chim. Acta., vol. 39, No. 24 (1956).
Rye, et al., "Stable Fluorescent Examples of Double–Stranded DNA", Nucl. Acids. Res., vol. 20, No. 11, pp. 2803–2812 (1992).
"PCR Protocols", ed. by Innis, et al.; Academic Press, 1990.
W. Forest et al., "New Methods of Preparative Organic Chemistry", vol. II, Acad. Press, 1963.

Primary Examiner—Kenneth R. Horlick
Attorney, Agent, or Firm—Fitzpatrick, Cella, Harper & Scinto

[57] ABSTRACT

A PCR amplification product is detected, in quantitative determination of nucleic acid and measurement of the number of bacterial cells or specific genes, by addition of a dye compound which does not fluoresce in the free state but fluoresces in the bonded state to a double-stranded nucleic acid.

59 Claims, 7 Drawing Sheets

BLANK

NUCLEIC ACID DETERMINATION EMPLOYING PYRYLIUM DYE

BACKGROUND OF THE INVENTION

1. Field of the Invention

The present invention relates to a method of determination of nucleic acid by detecting the polymerase chain reaction (PCR) amplification product by use of a dye compound which does not fluoresce in the free state but fluoresces reacting with double-stranded nucleic acid. The present invention also relates to a method for measuring the number of microbial cells, the number of specified genes and the number of specified gene copies. The present invention further relates to a measuring-kit to be utilized for the above method. The method is useful for measuring the number of cells of a specified microorganism in a solution or in soil.

2. Related Background Art

The PCR is a method for enzymatically amplifying a specific DNA sequence by using the specified sequence as a template defined with two kinds of primers. This method has become utilized in detection of nucleic acid. Detection is conducted by the steps of selecting a specific sequence of the target nucleic acid, preparing a set of primers for amplifying a specific sequence, conducting PCR by utilizing the target nucleic acid as a template, and detecting the amplified specific sequence. According to PCR, the specific sequence which is characteristic of the object to be detected is amplified with a high amplification rate, enabling the detection of even a minute amount of target nucleic acid in a sample. For example, the reaction for several hours can give about 1,000,000-fold amplification. Therefore, even one molecule of nucleic acid can be detected by PCR. This amplification proceeds only when the two primer sequences are complementary to the template nucleic acid, and no amplification product can be obtained when the complementary sequence is not present.

Thus, PCR, which greatly improves the sensitivity of nucleic acid detection, has come to be utilized to detect nucleic acid in various technical fields in place of the hybridization method: particularly, to identify the pathogen of a virus- or bacterial disease in clinical tests, to analyze genes in genetic disorders, and to detect gene markers in cancer diagnosis.

Another application of PCR is in measurement of the cell number of a certain microorganism, which is conducted with combination of PCR with MPN (most probable number) method, [H. O. Halvorson, and N. R. Ziegler: J. Bacteriol., 25 101 (1933)]. In MPN method, which is also called the dilution count method, a sample is serially diluted, a predetermined portion of each sample dilution is inoculated into a culture medium in a test tube, and incubated for a sufficient period, thereafter occurrence of cell growth is observed for each tube, and the statistic treatment of the result gives the most probable cell number of the specimen ("Dojobiseibutsu Jikkenho (Experiment in soil microbiology)", page 45, published by Yokendo Co.). This method has disadvantages that the procedure is troublesome and requires many test tools and long incubation period especially for soil microorganism determination. Moreover, by MPN method, the number of the specific microbial cells cannot be determined when two or more kinds of microorganisms are present in the sample, since the MPN method is positive for all the microorganisms grown in the employed culture medium. To offset such disadvantages, trials have been made to detect a microorganism by the DNA level using DNA amplification. One method therefor is a combination of PCR with MPN. In this PCR-MPN combination method, DNA is extracted from a sample containing the target microorganism, the extracted DNA is serially diluted, the dilutions are subjected to PCR with two kinds of primers to amplify the nucleic acid sequence characteristic of the target microorganism, and the number of the target microbial cells is determined by detecting the amplification product.

PCR amplification gives the product DNA in an amount of micrograms from picograms of starting DNA in a short time, which enables rapid in vitro amplification of cloned DNA or genome DNA in a large amount. Thus, the PCR is now being applied to cloning and various detections. In PCR, the target double-stranded DNA is denaturated by heating to give single-stranded DNA, and the primers anneal to each of the single-stranded DNA which serves as the template, and a complementary strand is synthesized by extending the primer with DNA polymerase. Therefore, theoretically, one strand of template DNA is required for amplification. When genome DNA is employed as a template DNA, the length of the single-stranded template DNA greatly varies depending on the kind of the source organism. For example, the human genome DNA has a length of $10^3$ times that of *Escherichia coli*. Thus, the number of DNA strands in one picogram differs by several numerical orders depending on the kind of the source organism.

The MPN-PCR method detects the number of DNA based on the above quantitative characteristics. In this method, the target DNA is serially diluted to the extent that a certain dilution provides only one molecule of DNA or none in the reaction system, and then the DNA is amplified and detected to determine the number of the template DNA molecules in the original sample by probability technique. Accordingly, this MPN-PCR method utilizes the principle of the MPN method of measurement of microbial cell number replacing the microorganism in MPN method with the template DNA, and the growth of the microorganism with PCR. In other words, in MPN, a sample containing microbial cells is serially diluted to such a concentration that one cell is present or not present in a certain volume of a dilution, then incubated for cell proliferation detection. The number of the cells in the starting sample is estimated from the results using probability technique. In the MPN-PCR method, the microorganism is replaced with template DNA, and the incubation process with PCR. Accordingly, in the MPN-PCR method, the object of the measurement is not the quantity of the target DNA, but the number of DNA molecules.

An example of the conventional MPN-PCR method is described specifically below. DNA extracted from a microorganism-containing sample is serially diluted to prepare decimal dilutions (e.g., dilution rate of 1, $10^{-1}$, $10^{-2}$, . . . , $10^{-9}$). Here, the dilution rate $10^n$ means that the sample is diluted to contain $1/10^n$ of the original sample. The respective dilutions (10 dilutions in this case) are subjected to PCR to amplify the target DNA. After the PCR, the reaction solution is subjected to agarose gel electrophoresis to detect the amplification product as an electrophoresis band. In a series of the dilutions, the band of the amplification product becomes undetectable at a certain dilution and thereafter. For example, if the amplification product is detected at the dilution rate of $10^{-5}$ and dilutions lower than that, PCR is carried out for the highest dilution in which the product was detected and two adjacent dilutions, namely the dilutions of $10^{-4}$, $10^{-5}$, and $10^{-6}$, in quintuplicate (15 samples in total), followed by agarose gel electrophoresis to detect the amplification product. The number of the samples positive for the amplification product in quintuplicate at the respective dilution is compared with the MPN table shown later (cited from *J. Bacteriol.*, 25 101 (1933), page 400), from which the most probable number is obtained. In this example, if 5 reactions of $10^{-4}$ dilution are all positive (namely, amplification product being detected), 3 out of 5 reactions of the 10–5 dilution are positive, and 1 out of 5 reactions of the $10^{-6}$ dilution is positive, from the numerals of 5, 3, and 1, a value (1.1) is obtained by applying 5, 3, and 1 to $P_1$, $P_2$, and $P_3$ in the MPN table. This value (1.1) multiplied by the reciprocal of $10^{-5}$ which is the highest dilution detected for the PCR amplification product, namely $1.1 \times 10^5$, is the number of the target DNA in the original sample DNA.

Assuming that one molecule of the target template DNA exists in one cell, the number of the template DNA measured by the MPN-PCR method is equal to the number of the cells in the sample from which the sample DNA was prepared. When the target gene belongs to a genome, however, several copies may exist for one gene. In such a case, it is necessary to determine the correlation between the cell number and the number of the DNA preliminarily since the number of DNA does not directly correspond to the cell number. Furthermore, the DNA extraction efficiency also needs to be taken into account. Therefore, for a precise measurement result, it is desirable to draw a calibration curve. This method is also applicable to the quantitative determination of the cells having plural copies of a specific gene due to the amplification as in the cancer cell.

The amplification product of PCR is conventionally detected, for example, by developing the PCR reaction mixture by gel electrophoresis to separate the amplification product from the other components such as the template nucleic acid and the primers, identifying the fluorescence-stained band of the amplification product in consideration of its molecular weight, and measuring the fluorescence intensity.

The PCR reaction mixture contains also the template nucleic acid, excess amounts of primers, etc. Therefore, the separation of the amplification product from other non-target components by gel electrophoresis becomes difficult depending on the nature of the nucleotide sequence of the target DNA. Moreover, when there are many test samples, it is laborious and time-consuming to carry out complicated electrophoresis, which lowers the efficiency of the detection operation. Therefore, the conventional techniques are not sufficient enough for especially gene analysis in the clinical examination where many samples should be treated with high efficiency.

In the application of PCR to MPN method, in order to estimate the precise number of the microbial cells, the samples are serially diluted by ten-fold, each dilution is PCR amplified, and the experiment is repeated for three serial decimal dilutions including the highest dilution in which the amplification product has been detected. Since this method estimates the cell number based on probability, usually at least 5 to 10 repetitions for each dilution level are required to meet the conditions for the estimation of the cell number on the basis of probability from the MPN table. Accordingly, at least about 25 PCR products for one sample should be subjected to gel electrophoresis, which means a lot of labor, complicated operations, and time to obtain the result.

As mentioned above, detection of nucleic acid or measurement of microbial cell number by PCR requires, in many cases, complicated and time-consuming operations to detect or determine the amplification products after the amplification reactions, hindering efficient treatment of a large number of samples. Therefore, a simple and precise method is strongly desired for detection and determination of PCR amplification products.

The most troublesome operation in detecting PCR amplification product is the gel electrophoresis to separate the amplification product from the primers added to the reaction solution in large excess. Various methods are investigated to omit the separation operation. Of the methods, noteworthy is a method employing a fluorescent intercalating agent (an intercalator) which increases fluorescence intensity when bound to double-stranded nucleic acid. In this method, the fluorescent intercalator reacts with the double-stranded nucleic acid which has been amplified by PCR, and the increase of fluorescence intensity caused by the reaction is measured to detect the amplification product. Theoretically, in this method the primer (single-stranded DNA) does not increase the fluorescence intensity of the intercalator. Therefore, this method advantageously saves the troublesome separation operation.

Japanese Patent Application Laid-Open No. 5-237000, for example, discloses use of a dye, as the fluorescent intercalator, such as ethidium bromide, acridine orange, bisbenzimide, diaminophenylindole, actinomycin, thiazole orange, chromomycin, and derivatives thereof for detection of the PCR amplification product. Of these dyes, ethidium bromide is preferred of which fluorescence intensity increases as much as about 50-fold under UV excitation light when bound to double-stranded nucleic acid, and about 20-fold under visible excitation light, in comparison with that in the free state (before the reaction with the double-stranded nucleic acid).

However, the dyes mentioned in the above Japanese Patent Application Laid-Open No. 5-237000 exhibit fluorescence even in the free state. The measured fluorescence thus includes both the fluorescence produced by the double-stranded nucleic acid-dye complex and that of the free dye. Therefore, the fluorescence of the free dye should be subtracted as the blank value from the measured value. In other words, in this method, the measured value does not give directly the presence or the quantity of the amplification product, and the blank value should be subtracted therefrom. When the amount of the amplification product is small, the increase of fluorescence intensity from the blank value may be small, and the sensitivity of the detection becomes inevitably low.

YOYO-1 (Nucleic Acids Research, 20 (11), 2803–2812 (1992)) emit little fluorescence in the free state, but when intercalated into double stranded DNA, a large increase of fluorescence intensity (about 3000-fold) will occur. With this dye, the above disadvantage of a high blank value can be offset. This dye, however, is not practically useful because it decomposes at room temperature. Moreover, this dye also detects the higher-order structure formed between the primers, as mentioned later, which disadvantageously prevents precise quantitative determination.

From the above viewpoint, in the above Japanese Patent Application Laid-Open No. 5-237000, the amplification cycle is continued till a sufficient fluorescent intensity is obtained in comparison with the blank value: the number of necessary cycles is in reverse proportion to the initial concentration of the target nucleic acid. In the determination of a target nucleic acid in the specification of the above patent application, the change of the fluorescence intensity is monitored in the course of the PCR amplification, and the initial concentration of the target nucleic acid is determined from the cycle number at which the fluorescence intensity changed abruptly.

Such a method of determination requires a troublesome operation of monitoring the fluorescence intensity in each cycle of the PCR reaction. Moreover, it is sometimes difficult to detect the point of the significant change of the fluorescence intensity. Therefore, the method still has problems in efficiency and sensitivity for quantitative determination of the target nucleic acid.

When the PCR amplification product is detected with ethidium bromide (EB) or the like, it is theoretically possible to detect the amplification product in the reaction mixture in the presence of the primer set, since the fluorescence intensity does not increase on reaction with primers. However, according to the studies by the inventors of the present invention, primers react with each other during the PCR to form aggregates (higher order structures having a three-dimensional structure) which is also detected with ethidium bromide or the like. If the amplification product is formed in a much larger amount than the higher-order structured primers, no problems arise. If not, the ratio of the fluorescence due to the higher-order structure matter in the measured fluorescence becomes larger, which presents precise quantitative determination. The amount of the higher-order structured matter is not steady since it becomes small when the amplification products are formed in overwhelming amounts, while it tends to be formed more when a little or no amplification product is formed. Therefore, the correction by comparison with the blank value is not easy.

The formation of the higher-order structured matter can be confirmed, for example, by conducting PCR in the absence of template nucleic acid, developing the reaction mixture by gel electrophoresis, and observing a cloud-like pattern stained with ethidium bromide in the low molecular weight zone.

The measurement error caused by the higher-order structure is ascribable to the PCR itself, and is liable to be more significant when the amplification is conducted for more cycles with a lower initial concentration of the target nucleic acid.

Accordingly, the conventional methods of determination of amplification product as described above are still insufficient for higher sensitivity.

The measurement of microbial cells by combination of MPN with PCR also involves the same problem of formation of the higher-ordered structure matter from the primers, inviting large determination error.

SUMMARY OF THE INVENTION

The present invention intends to provide a method for precise determination of a PCR amplification product in a simple operation.

The present invention also intends to provide a method for measuring the number of target microorganism or cells, the number of a specified gene, or the copy number of a specified gene.

The present invention also intends to provide a measuring kit for the above methods.

The method to determine the nucleic acid quantity of the present invention comprises conducting PCR on the sample nucleic acid using a primer set which is necessary to amplify a specified sequence region of the target nucleic acid, then reacting the double-stranded amplification product which is formed when the target nucleic acid is present in the sample, with a dye compound which does not fluoresce in the free state but fluoresces when reacted with the double-stranded nucleic acid, followed by measuring the fluorescence intensity to determine the quantity of the target nucleic acid in the sample.

The measuring kit for the nucleic acid determination of the present invention comprises a reactor in which a necessary amount of a dye compound which does not fluoresce in the free state but fluoresces when reacted with double-stranded nucleic acid is placed in a PCR reaction chamber. This measuring kit may contain in the reaction chamber a necessary amount of a primer set required for PCR to amplify a specified sequence region of the target nucleic acid. The measuring kit may have a PCR reaction chamber and separated from it, a reagent chamber wherein a necessary amount of a dye compound which does not fluoresce in the free state but fluoresces when reacted with double-stranded nucleic acid is placed so as to be fed to the reaction chamber. This kit also may contain in the reaction chamber a necessary amount of a primer set required for PCR amplification of the specified sequence region of the target nucleic acid.

The method for measuring the number of a target microorganism or cells, the number of a specific gene, or the copy number of a specific gene comprises extracting the nucleic acid from a sample containing a microorganism or cells to be detected, preparing serial dilutions of the extracted nucleic acid, conducting PCR on the diluted samples to amplify a sequence which is characteristic of the microorganism or the cells, reacting the resulting amplified double-stranded product with a dye compound which does not fluoresce in the free state but fluoresces in the bonded state to the double-stranded nucleic acid, measuring the intensity of the fluorescence, and deriving the number of the microorganism or the cells, the specified genes, or copies of the specified gene from the dilution where the fluorescence was observed.

The measuring kit used for the above measurement comprises a reactor having a plurality of reaction chambers for PCR and containing therein a required amount of a dye compound which does not fluoresce in the free state but fluoresces when in the bonded state to double-stranded nucleic acid, the reaction chambers can be employed for serial dilution of nucleic acid sample extracted from a sample containing target microorganism or cells, as well as the PCR of each dilution for amplification of a sequence which is characteristic of the target microorganism or cells. The each reaction chamber of the kit may further contain a primer set for PCR of the sequence characteristic of the target microorganism or cells.

The present invention mentioned above is applicable also to an MPN-PCR method as described later.

DETAILED DESCRIPTION OF THE PREFERRED EMBODIMENTS

Figure 1:
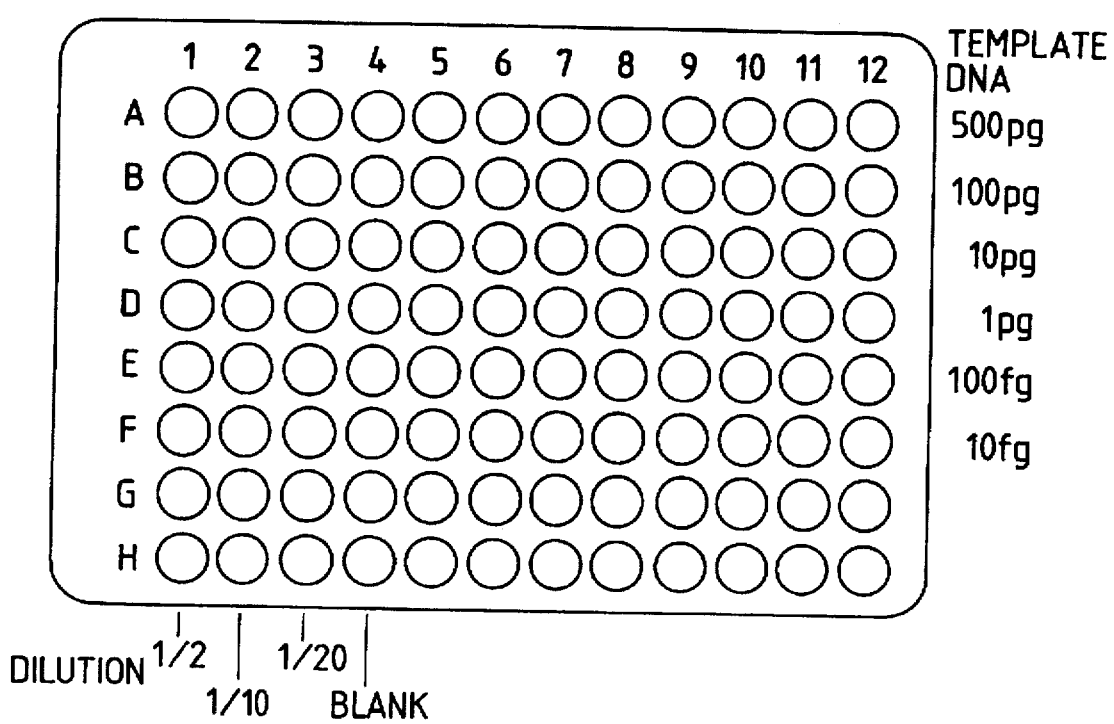
FIG. 1 illustrates an arrangement of samples prepared in Example 1 on a microplate.

The dye compound employed in the present invention does not fluoresces in the free state but fluoresces when reacted with double-stranded nucleic acid. Reaction of the dye compound with double-stranded nucleic acid means specific insertion of the dye compound into grooves of a stable double helix structure of double-stranded nucleic acid to bind thereto. In that state, the dye compound fluoresces on irradiation of excitation light. The dye compound does not fluoresce in the free state. i.e., in the separated state, on irradiation of excitation light.

This dye compound does not readily enter short double-stranded portions of primers which do not form stable double helix structure. Even if it enters that portion, it produces no fluorescence, that is, it fluoresces only in the bonded state to the stable double helix structure. Accordingly, the dye compound of the present invention is the one which enters a main groove or a sub groove of a double helix structure and links thereto, producing fluorescence in that state. The use of a dye compound having such characteristics enables precise and selective detection of the amplification product by simply adding directly the dye compound to a PCR reaction mixture without separating the amplification product from the primers and template nucleic acid. The fluorescence of the dye compound in the free state may be negligibly weak.

The dye compound is exemplified by DAPI (4',6-diamino-2-phenylindole dihydrochloride), Hoechst 33258 (trade name), Hoechst 33342 (trade name), pyrylium compound salts and other salts analogous thereto represented by the general formula [I] below:

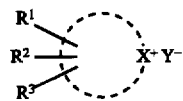

[I]

where

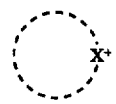

represents a heterocycle, and X is O, S, Se, or Te, the heterocycle including a five-membered and six-membered ring such as a pyrylium ring and pyrylium-analogous ring; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl group; $R^3$ is a group of —A or —L—A wherein L is —$L^1$—, —$L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—

($R^4$ representing a cyclic structure having an oxo group). The bivalent group derived from a substituted or unsubstituted aryl group includes a phenylene group and the like, and may have the bonds in any of ortho, meta, and para positions. The lower alkylene group includes linear or branched alkylene group having 1 to 4 carbons, the substituent including groups of —L—A. The cyclic structure having an oxo group includes a heterocycle, aromatic ring, and aliphatic ring having at least an oxo group.

The group —L— preferably includes those represented by the general formulas [II], [III], [IV], [V], and [VI] below:

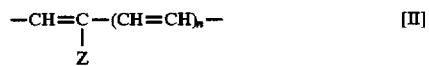

[II]

where Z is a hydrogen atom, or a substituted or unsubstituted lower alkyl group; and n is 0, 1, or 2, and the substituent for the alkyl group is exemplified by —L—A defined above;

[III]

where n is 0, 1, or 2, and Φ is a substituted or unsubstituted o-, m,- or p-phenylene.

[IV]

where Φ is a substituted or unsubstituted o-, m-, or p-phenylene group;

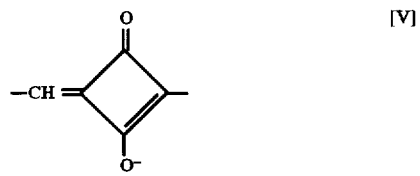

[V]

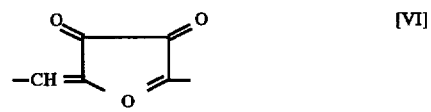

[VI]

In the above general formulas, the substituent of the phenylene includes the groups mentioned above.

The group A in $R^3$ in General Formula [I] is a substituted or unsubstituted aryl, or —CH=$R^5$ ($R^5$ being a substituted or unsubstituted heterocycle, a substituted or unsubstituted cycloalkyl, or a substituted or unsubstituted aromatic ring). The heterocycle for $R^5$ includes the ones derived from the groups shown below:

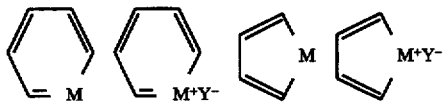

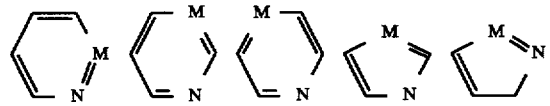

where M and N are independently an oxygen atom, a sulfur atom, or a nitrogen atom, and $Y^-$ is an anion. The substituent therefor includes a substituted or unsubstituted aryl group. The substituted or unsubstituted cycloalkyl group may be saturated or unsaturated and includes the ones derived from the groups below capable of constituting a resonance system:

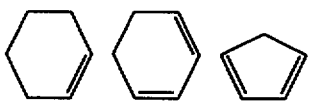

The substituted or unsubstituted aromatic ring includes an azulene ring. The substituent linked to the above groups includes lower alkyl groups, and substituted or unsubstituted aryl groups.

In the pyrylium ring or an analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group.

$Y^-$ is an anion, including $BF_4^-$, perchlorate ion, $HO_3SCH_2COO^-$, halide ion such as chloride ion, bromide ion, iodide ion, and fluoride ion, a compound functioning as an anion such as aliphatic sulfonates and aromatic sulfonates, and complex ions of transition metals such as Zn, Ni, Cu, Pt, Co, and Pd.

When the above substituent is further substituted by a halogen, the halogen includes Cl, Br, and I. The lower alkyl group may be linear or branched, and is preferably 1 to 4 carbons. The aryl group includes a phenyl group or the like. The substituent of the aryl or phenylene group includes an amino group substituted with a lower alkyl group (loweralkylamino group). Such a lower-alkyl amino group include preferably dimethylamino, diethylamino, or the like at a para position. The lower aralkyl group includes lower alkyl groups substituted by the aforementioned substituted or unsubstituted aryl.

Of the compounds represented by General Formula [I], the X-containing heterocycle is preferably substituted by two or more substituted or unsubstituted aryl groups. The examples of such compounds having six-membered heterocycle are:

(1) those having substituted or unsubstituted aryl groups at 2- and 4-positions and an $R^3$ group at any one of 3-, 5-, and 6-positions of the X-containing six-membered ring;
(2) those having substituted or unsubstituted aryl groups at 3- and 5-positions and an $R^3$ group at any one of 2-, 4-, and 6-positions of the X-containing six-membered ring; and
(3) those having substituted or unsubstituted aryl groups at 2- and 6-positions and an $R^3$ group at any one of 3-, 4-, and 5-positions of the X-containing six-membered ring.

The introduction of substituted or unsubstituted aryl groups to such positions is preferred to obtain satisfactory properties as an intercalator in a nucleic acid base pair. Additionally, the X-containing heterocycle is preferably substituted by two or more substituted or unsubstituted aryl groups such that the substituting positions are not adjacent to each other.

Specific examples of the compound of General Formula [I] are shown later in Table 1. Of these, particularly preferred are 2,4-bis(N,N,-dimethylaminophenyl)-6-methylpyrylium salts and 2,4-bis(N,N,-dimethylaminophenyl)-6-methylthiopyrylium salts represented by General Formula [VII]:

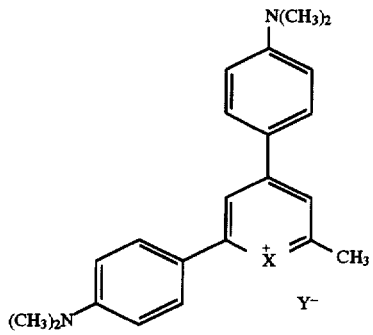

where X is O or S, and $Y^-$ is an anion. These compounds are preferred because of their very high intensity of fluorescence in the inserted state into double-stranded nucleic acid.

The dye compound employed in the present invention reacts selectively with the stable double-stranded helix DNA to produce fluorescence. Therefore, even if the dye compound is incorporated in a higher-order structure formed by the aforementioned reaction from primers, the compound does not fluoresce because the double-stranded portion of the higher-order structure is not a stable double-stranded structure.

The compound of General Formula [I] is introduced specifically into the double-stranded structure in a ratio of one molecule to 20 to 30 base pairs. The compound is advantageously not liable to be inserted into the higher-order structure derived from primers as mentioned above. Further, when the compound of General Formula [I] is incorporated into a double-stranded nucleic acid segment having a sequence to be amplified, the incorporation density is much lower than that of ethidium bromide or the like, so that the elevation of melting temperature (Tm) of the double-stranded nucleic acid hardly occurs not affecting the PCR. Because of the low incorporation density, when the PCR product is analyzed by gel electrophoresis, the mobility of the double-stranded nucleic acid is hardly affected by the incorporated dye compound, thus enabling precise size measurement.

To the contrary, a conventionally used fluorescent intercalator such as ethidium bromide, acridine orange, and YOYO-1 is inserted into the double-stranded nucleic acid at a ratio of one molecule to several base pairs (about 2 to about 5 base pairs). These dyes are incorporated into the double-strand portion of the aforementioned higher-order structure formed from the primers, which causes increase of undesired fluorescence. Also these dyes greatly affect Tm of the double-stranded nucleic acid and the mobility thereof in gel electrophoresis because of the high incorporation rate into the target double-stranded nucleic acid.

To conduct precise quantitative determination by utilizing the above benefit of the dye compounds in the present invention, the amplification product is desired to form a stable double helix structure. Therefore the present invention is useful when the amplification products have a length of 100 base pairs or more, for example, preferably 300 base pairs. The maximum length of the amplification product is not particularly limited. The velocity of incorporation of the nucleotide in PCR is said to 35 to 100 nucleotides per second, for example, at 72° C. The rate depends on the reaction conditions such as pH and salt concentration of the reaction medium, and the base sequence of the target nucleic acid. Accordingly, when the reaction time of each cycle of PCR is one minute, the length is preferably not more than 2000 base pairs. In addition, since byproducts tend to be formed when the chain length is excessively long, it is preferable that the length is not more than 1000 base pairs ("PCR Protocols", edited by Michael A. Innis, David H. Gelland, John J. Shinsky, and Thomas J. White, 1990, (Academic Press Inc., San Diego, Calif. 92101)).

In the PCR, a primer set which is capable of defining the intended specific region of the target nucleic acid is used according to the purpose. The primer is required to have a sufficient length for recognizing the specific sequence at the end of the specific region to be amplified of the template nucleic acid, but should not be unnecessarily long, since excessively long primers tend to form locally a double-stranded structure between the primers. Therefore, the length of the primer is less than about 30 base pairs, preferably less than about 28 base pairs. The minimum of the primer length is not specially limited, but is required to have a sufficient length for recognizing the terminal portion of the specific region to be amplified: e.g., not less than 14 base pairs, preferably not less than 18 base pairs.

In the quantitative determination of nucleic acid of the present invention, firstly a sequence region is specified which is characteristic of the target nucleic acid to be determined. Secondly, PCR is conducted using a primer set necessary for amplification of the specified sequence region and the target nucleic acid as the template. Subsequently, the resulting amplified product is reacted with a dye compound having the aforementioned properties, and the intensity of the fluorescence is measured with irradiation of excitation light. The intensity of the fluorescence is proportional to the initial concentration of the template (the concentration before the PCR) provided that the concentrations of the reaction components are selected suitably. Therefore, the target nucleic acid in an unknown sample can be determined by conducting PCR and then measuring the fluorescence intensity by reference to a calibration curve prepared preliminarily for the fluorescence intensity as a function of the template concentration.

The quantitative determination can be conducted simply by use of a calibration curve as mentioned above with a reaction system for which the optimum condition has been established. The reaction conditions, however, especially the amount of the target nucleic acid, the amount of the primers, the reaction temperature, etc. depend on the respective reaction systems. Therefore, when the optimum reaction conditions for calibration curve preparation are unknown, complicated operations are necessary for establishing the conditions.

When the conditions for calibration curve preparation are not established in the system, the approximate quantity of the target nucleic acid can be measured by simply preparing serial dilutions of the nucleic acid of an unknown sample, conducting PCR with the diluted samples, and determining the target nucleic acid segment by use of an MPN-PCR method which gives probability of detection of the target nucleic acid segments. Thereby the conditions for preparing the calibration curve can be obtained easily. For instance, in the specific example described before in the Related Background Art, the number of the template DNA in the sample is $1.1 \times 10^5$, and at $10^{-5}$ dilution, three samples out of the five samples are positive. In this case, at the concentrations of $10^{-4}$ dilution or higher, all of the five tests of each concentration will be positive. In this example, firstly the concentration range including the critical dilution of the template DNA is determined according to the presence or absence of the amplification product, and then detailed MPN investigation is conducted on the concentration region. This is because, in agarose gel electrophoresis, the detection is conducted in an ON/OFF manner, the presence or absence of the band, and even when the DNA is quantitatively detected by fluorescence staining, the quantitation is not sufficient in spite of the complicated operations. On the other hand, the method of the present invention employing an MPN-PCR method as described later makes it practicable to check the formation of amplification product for all over the dilutions, by use of a tool such as a microplate which can provide many reaction zones (chambers). For instance, when the sample described in the Related Background Art is treated on a microplate according to the present invention, positive wells and negative wells will be observed at the $10^{-5}$ dilution, while at the lower dilution levels, $10^{-4}$ dilution or lower, the same intensity of fluorescence will be observed in the same dilution level, because the amplification proceeds in the same degree in the same dilution level. The plots of the average fluorescence intensity of the five reaction of respective dilution as a function of dilution levels will give a straight line. The longer the straight line region, the more appropriate is the PCR conditions. If the plots deviate significantly from the straight line, it means that the quantity of the primer or other conditions need to be changed.

If the fluorescence intensity is in a linear relation with the dilutions, the number of the template DNA and the quantity thereof (number×molecular weight) can be determined quantitatively from this calibration line since the number of the template DNA is known in this MPN-PCR.

As described above, the method of the present invention enables direct and selective measurement of the fluorescence which is produced only when the amplified product reacted with a dye compound added to the PCR mixture. Therefore, the separation of the amplified product from the primer and the template is unnecessary and even when the higher-order structure are formed between the primers, the influence of it on the measurement result is negligible. Accordingly, the fluorescence intensity obtained by directly adding the dye compound to the reaction mixture can be used for calculation of the precise quantitative determination. When ethidium bromide or a similar substance which fluoresces even in the free state is used for the quantitative determination the blank value has to be subtracted from the measured value. Since the blank value varies depending on the measuring conditions, the determination conditions have to be decided in consideration of the relation of the blank value to the measured value for each of measurement conditions, which is quite troublesome. In the method of the present invention, such blank value consideration or a set up of determination conditions is not necessary, differing from with ethidium bromide, since the dye compound of the present invention produces no or negligible fluorescence in the free state. Further in the present invention, the fluorescence intensity need not be monitored during the PCR process as described in Japanese Patent Application Laid-Open No. 5-237000.

Furthermore in the present invention, a microplate may conveniently be used for the detection by transferring the PCR reaction mixture from the reaction vessel to the microplate well and measuring the fluorescence by use of a microplate fluorescence detector (reader), conveniently requiring a small amount of a reagent and a short measurement time. The PCR process itself may be conducted on the microplate, which more simplifies the determination operation.

A nucleic acid determining kit can be provided by employing a reactor like a microplate having many wells as reaction chambers and placing a necessary amount of a dye compound of the present invention by applying a solution thereof to each of the reaction chambers, followed by evaporation or drying or the like. Such a constitution is practicable owing to the stability of the dye compound at room temperature.

Another type of kit is also useful in which reagent chambers are provided separately from the PCR reaction chambers, and the dye compound of the present invention placed in the reagent chambers is added to the reaction chambers in the PCR step. The dye compound may be placed in the reagent chamber as a solution. If the dye compound is water-soluble, it may be solubilized in a suitable buffer solution, and if the compound is soluble in an organic solvent, the compound may be placed as a solvent solution.

The reagent chamber may contain a buffer solution, nucleotides, the enzyme, etc. necessary for the PCR together with the dye compound. When all of these PCR substances are dissolved in an aqueous solution, the organic solvent for the water-insoluble dye compound is preferably not more than 1% based on the aqueous solution. This constitution of placing the reagents for PCR and the dye compound together in a reagent chamber is possible because the dye compound of the present invention is incorporated into the double-stranded nucleic acid segments (amplification product) at much lower density than ethidium bromide, resulting in little elevation of the melting temperature (Tm), thus hardly affecting PCR reaction efficiency.

Figure 9A:
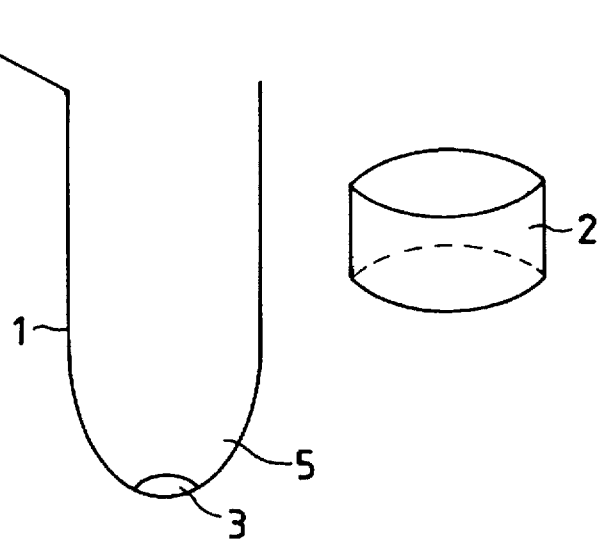
FIGS. 9A to 9C show the construction and the method of use of a nucleic acid-detecting kit of the present invention.
Figure 9B:
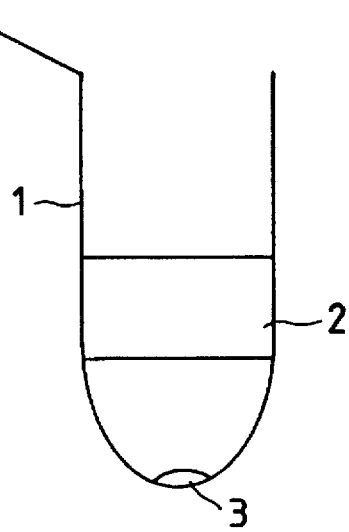
Figure 9C:
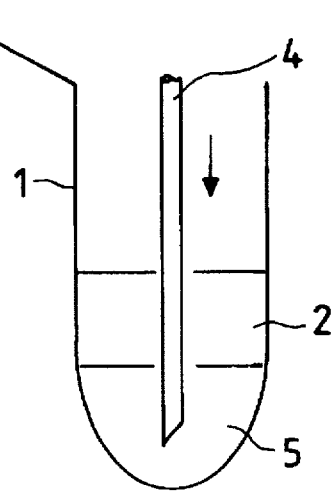

FIGS. 9A to 9C show an example of constitution of the kit having such a reactor. In an appropriate container 1 which forms a reaction chamber 5, primer 3 is placed by liquid application or a like method, and further a container 2 is placed in it as the reagent chamber which is made of paraffin-coated paper or the like to be liquid-tight, and in which packed is a solution containing the enzyme, nucleotides, a buffer solution, etc in an amount necessary for the PCR (see FIG. 9A and FIG. 9B). With this device, PCR is conducted by injecting a solution of template nucleic acid into the reaction chamber 5 by a suitable means such as a Pipetman, concomitantly breaking through the container 2 to feed the contents therein to the reaction chamber 5, and mixing the reaction components to start PCR (see FIG. 9C). The dye compound for detection of the amplified product may be added after the PCR, or may be placed preliminarily in the reaction chamber. Otherwise, the dye compound may be contained in the solution in the reagent chamber 2.

Two or more reagent chambers may be provided for storing separately the reaction components.

The dye compound may be added to the reaction chamber for PCR prior to or after the PCR. In the latter case, another reagent chamber may be provided in which a necessary amount of the dye compound is held, and the dye compound may be added to the reaction chamber after the PCR from the reagent chamber. Of the compounds represented by General Formula [I], water insoluble ones remain undissolved, even if they are placed in the reaction chamber during the PCR, and the compounds are allowed to react after the PCR by addition of a suitable solvent to the reaction chamber. The water-insolubility of the compound eliminates the undesirable influence of the compound on PCR, even though in general such effect is inherently small for the compounds of General Formula [I]. The suitable solvent used therefor includes acetonitrile, ethanol, dimethylsulfoxide (DMSO), etc. The operation of PCR in the reaction chamber can be simplified by placing the primer separately and preliminarily in the reactor by liquid application or in a powder state.

The detection of the amplification product of PCR with the dye compound of the present invention is suitably conducted by MPN utilizing PCR (MPN-PCR method). This method enables measurement of the number of individuals of microorganisms, animal cells, human cells, vegetable cells, etc. (the number of cells, the number of bacteria, the number of mycelia, etc.), and the number of specific genes or the number of copies of the specific gene of the above individuals with greatly simplified operations.

An example of the MPN-PCR method is described below for measurement of the number of individuals of a microorganism (cell number).

A soil sample is treated to extract the nucleic acid of microorganisms in soil. For example, to a soil sample (1 g), a phosphate buffer solution (1 ml) is added, and the mixture is agitated by a vortex mixer twice for 20 seconds each. Thereto 1/10 volume of 10% SDS was added, and the mixture is vortexed again. The resulting mixture is kept at 70° C. for one hour for cell lysis. Then the soil is removed by centrifugation to collect the supernatant as the nucleic acid fraction. Thereto, 1/5 volume of 7.5M sodium acetate is added, and the mixture is left standing at 4° C. for 5 minutes. The supernatant (1 ml) is recovered, and thereto, isopropanol (4/5 volume) is added. The nucleic acid fraction is recovered by centrifugation, and dissolved in a TE buffer solution (0.1 ml). DNA is recovered therefrom after RNase treatment.

An aliquot of the recovered DNA is diluted 100-fold. Starting from it, a series of dilutions was prepared to make $10^{-1}$ to $10^{-8}$ dilutions. These dilutions are placed in the sample block A on the microplate. More specifically, the $10^{-1}$-dilution of the starting DNA solution (100-fold diluted soil extract), is placed in A1 to A5 wells, the $10^{-2}$-dilution solution at the wells B1 to B5, and so forth, and $10^{-8}$-dilution solution at the wells H1 to H5. Then a reaction solution containing reagents (a nucleotide, a primer salt, a Taq polymerase, etc.) necessary for PCR are added to all the wells including the blanks to allow the PCR to proceed. After the reaction, the fluorescence intensity of respective wells are measured by use of a dye compound. For example, the well which fluoresces at an intensity of twice or more that of the blank value is defined to be positive, and the dilution limit for the positive fluorescence is derived. If the numbers of positive samples out of the 5 samples at each of the dilution level (positive sample number/total sample number) are 5/5 at $10^{-4}$ dilution, 3/5 at $10^{-5}$ dilution, and 0/5 at $10^{-6}$ dilution, the critical dilution for the positive fluorescence is $10^{-5}$. The numbers of the positive samples (5, 3, and 0) at these dilution degrees are respectively applied to $P_1$, $P_2$, and $P_3$ shown in the MPN table shown later (cited partially, for serial decimal dilutions in quintuplicate, from J. Bacteriol. 25 101 (1933), page 400, "III. MPN (Most Probable Number) Table", thereby the most probable number of 0.79 is read from $P_1=5$, $P_2=3$, and $P_3=0$. This value is the number of the template DNA derived by a probabilistic statistical technique. By multiplying MPN with the reciprocal of the critical dilution degree and consideration of the initial dilution degree, the number of the template DNA contained in the soil is estimated as $0.79 \times 10^5 \times 10^2 = 0.79 \times 10^7$. This number of the template DNA itself is the number of the microorganism individuals (cell number) in 1 gram of the soil provided that the sequence of the template DNA is characteristic of the target microorganism in the soil and the sequence exists only one in number in one microbial cell. Naturally in this example, the highest dilution at which all the wells fluoresces reflects the number of the template nucleic acid. Therefrom, a calibration curve for the fluorescence intensity as the function of the number of the template DNA (or number of the individual microorganism) can be made.

TABLE 1

MPN (Most Probable Number),
for Serial decimal Dilution, in quintuplicate

| $P_1$ | $P_2$ | $P_3$ 0 | 1 | 2 | 3 | 4 | 5 |
|---|---|---|---|---|---|---|---|
| 5 | 0 | (0.23) | (0.31) | 0.43 | 0.58 | 0.76 | 0.95 |
| 5 | 1 | (0.33) | (0.46) | 0.64 | 0.84 | 1.1 | 1.3 |
| 5 | 2 | (0.49) | (0.70) | (0.95) | 1.2 | 1.5 | 1.8 |
| 5 | 3 | (0.79) | (1.1) | (1.4) | 1.8 | 2.1 | 2.5 |
| 5 | 4 | (1.3) | (1.7) | (2.2) | (2.8) | 3.5 | 4.3 |
| 5 | 5 | (2.4) | (3.5) | (5.4) | (9.2) | (16) | — |

In Table 1, the numbers in parentheses are of high reliability (probability L is 0.05 or lower). When a code without parentheses is obtained for the experimental results, the process of the experiment needs to be reconfirmed. The MPN table cited as Table 1 is a part of the MPN table of the aforementioned literature. If an experimental result falls outside Table 1, corresponding part of the original MPN table of the literature should be referred to. The literature includes MPN tables for various experimental conditions, which may be used according to the experiment conditions.

In the conventional MPN-PCR method in which PCR and agarose gel electrophoresis are combined as described in Related Background Art, two steps of PCR are conducted: the first PCR operation for determining the dilution limit for the positive reaction, and the second PCR operation to investigate the vicinity of the critical dilution in detail to obtain the most probable number of the individuals from the MPN table. For example, from the above-described soil sample (1 gram), DNA is recovered in the same manner as above. The recovered DNA, without the above-described first dilution, is serially diluted to the dilution degrees of from $10^{-1}$ to $10^{-9}$. The respective dilution solutions are subjected to the first PCR in a conventional manner, and the presence of the amplification product is detected by agarose gel electrophoresis to find that the dilutions are positive to the $10^{-7}$ dilution degree. Then 5 samples of the respective dilutions at $10^{-6}$, $10^{-7}$, and $10^{-8}$ dilution are again subjected to PCR. The positive numbers at each dilution are 5/5 for $10^{-6}$ dilution, 3/5 for $10^{-7}$ dilution, and 0/5 for $10^{-8}$ dilution. Therefore the value 0.79 is obtained from the MPN table in the same manner as above. The number of the template DNA in the soil is derived from this value multiplied by the reciprocal of the dilution degree of the dilution limit (0.79× $10^7$). This method, however, requires two series of operation of PCR and electrophoresis, and is troublesome. On the other hand, the method of the present invention gives the results directly by conducting one PCR operation without the electrophoresis operation, thereby the measurement operation being simplified greatly.

When the amplification product of PCR in the MPN-PCR method is detected with the aforementioned dye compound, the aforementioned operations and conditions can be employed in the determination of the PCR amplification product, as well as the aforementioned kit.

In the MPN-PCR method, use of a tool having a plurality of reaction chambers (wells) such as a microplate is preferred since simultaneous treatment of serially diluted samples is required for statistical treatment of the result. Even when PCR is conducted in different vessels, the microplate is preferably used for the detection of the amplification product with the dye compound.

This method for measuring the number of the template DNA is applicable effectively to measure the cell number of the target microorganism in a liquid or in soil, the number of microbial cells in various samples, the number of cells in various samples, the number of cells in various tissues, the number of a specified gene and copy number thereof in various living body samples, and so forth. Usually, the concentration of template DNA is estimated by weight based on the light absorption intensity. In the case of cancer cells, however, the number of the copies (the number of specified genes) is frequently of interest. In such a case, the method of the present invention is useful. The number of copies of a specified gene in a tissue can be estimated according to the present invention, irrespectively of the amount of the cells from which the nucleic acid is extracted, by measuring the number of a common gene in the same manner as described above, then measuring the number of a specified gene such as a oncogene, and deriving a ratio of the number of the specified gene and the number of the common gene which is common to normal cells and cancer cells.

This method is also useful for judging the presence of cancer cells in a human tissue. For this purpose, for example, the number of a specified gene common to all the cells constituting the tissue is estimated by this method, and the number of a specific gene characteristic to cancer cells to be detected is estimated for the same tissue sample.

REFERENCE EXAMPLE 1

100 ml of acetic anhydride and 30 ml of concentrated sulfuric acid were mixed with cooling, and the resulting mixture was kept at 80° C. for 3 hours. Thereto 20 ml of acetic anhydride and 30 ml of p-dimetylaminoacetophenone were added at room temperature. Then the mixture was stirred at 45° C. for 24 hours for reaction. An equal amount of ethanol was added thereto, and the mixture was cooled. Further thereto, aqueous potassium iodide solution was added to precipitate a crude crystalline matter. This crude crystalline matter was collected by filtration, and recrystallized from an ethanol-ether mixture (1:4 in volume ratio) to obtain 2-metal-4,6-bis-(4-N,N-dimetylaminophenyl) pyrylium iodide (Compound 1 in Table 2, where Y is I) in a green crystal form.

[Analysis Results of Obtained Compound 1 (Y:I)]

Melting point: 254°–257° C. UV/visible ($CH_3CN$, $\epsilon \times 10^{-4}$) λmax: 444 nm (2.43), 550 nm (8.24) NMR ($^1H$, DMSO) δppm: 8.3737 (1H, s), 8.2729 (1H, d, J=9.0 Hz), 8.1795 (1H, d, J=9.0 Hz), 7.8864 (1H, s), 6.9117 (4H, t, $J_{AB}=J_{BC}=9.77$), 3.1829 (6H, s), 3.1340 (6H, s), 2.6809 (3H, s) FAB mass m/z 333 IR (KBr) ν $cm^{-1}$: 1645, 1610(sh), 1580(s), 1490(s), 1270, 1200, 1160

2-methyl-4,6-bis-(4-N,N,-dimethylaminophenyl) pyrylium perchlorate (Compound 1 (Y: $ClO_4$)) was prepared in the same manner as above except that the aqueous potassium iodide was replaced by aqueous perchlorate solution.

REFERENCE EXAMPLE 2

20 Grams of sodium sulfide nonahydrate was dissolved in deionized water, and the total volume was adjusted to 50 ml. In this solution, 7 g of sodium hydrogen carbonate was dissolved. Further thereto, 50 ml of ethanol was added under cooling with ice. The mixture was stirred at room temperature for 30 minutes. The precipitated sodium carbonate was removed by filtration, and washed with 25 ml of ethanol. The filtrate and the washing were combined to obtain about 125 ml of a sodium hydrogen sulfide solution in ethanol.

0.92 Gram of 2-methyl-4,6-bis-(4-N,N-dimethylaminophenyl)pyrylium iodide prepared in Reference Example 1 was dissolved in 20 ml of DMSO. To the resulting solution, to which 5 ml of the above sodium hydrogen sulfide solution in water-ethanol was added. The mixture was stirred at room temperature for 5 minutes. Then 0.75 ml of hydroiodic acid was added and the mixture was stirred 5 minutes. Thereafter in a conventional manner, the mixture was extracted with dichloromethane, purified by silica gel column chromatography, and the product was recrystallized from a ethanol-ether mixed solvent (1:4 in volume ratio) to obtain 0.7 g of crystalline 2-methyl-4,6-bis-(4-N,N-dimethylaminophenyl)thiopyrylium iodide (Compound 2 in Table 2, where Y is I).

[Analysis Results of Obtained Compound 2 (Y:I)]

Melting point: 246°–248° C. UV/visible (CH$_3$CN, $\epsilon \times 10^{-4}$) $\lambda$max: 495 nm (2.50), 587 nm (4.95) NMR ($^1$H, DMSO) $\delta$ppm: 8.5679 (1H, s), 8.4323 (1H, s), 8.2436 (2H, d, J=9.27 Hz), 7.9786 (2H, d, J=9.28), 6.8959 (4H, t, J$_{AB}$=J$_{BC}$=9.28), 3.1756 (6H, s), 3.1157 (6H,s), 2.8323 (3H, s) FAB mass m/z 349 IR (Kbr) v cm$^{-1}$: 1600(s), 1560(s), 1640(s), 1430(s), 1370(s), 1260(s), 1160(s)

2-methyl-4,6-bis-(4-N,N,-dimethylaminophenyl)thiopyrylium perchlorate (Compound 2 (Y: ClO$_4$)) was prepared in the same manner as above except that the aqueous potassium iodide was replaced by an aqueous perchlorate solution.

REFERENCE EXAMPLE 3

Compounds 3 to 55 shown in Table 2 were prepared respectively. In Table 2, Φ represents a p-phenylene group, or a phenyl group.

TABLE 2

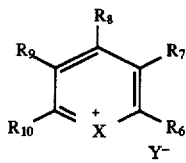

| Compound No. | X | Y | R$_i$ | L | A |
|---|---|---|---|---|---|
| 1 | O | ClO$_4$ or I | R$_6$ = CH$_3$<br>R$_7$ = H<br>R$_8$ = Φ-N(CH$_3$)$_2$<br>R$_9$ = H<br>R$_{10}$ = A | | Φ-N(CH$_3$)$_2$ |
| 2 | S | ClO$_4$ or I | R$_6$ = CH$_3$<br>R$_7$ = H<br>R$_8$ = Φ-N(CH$_3$)$_2$<br>R$_9$ = H<br>R$_{10}$ = A | | Φ-N(CH$_3$)$_2$ |
| 3 | O | ClO$_4$ or I | R$_6$ = Φ<br>R$_7$ = H<br>R$_8$ = A<br>R$_9$ = H<br>R$_{10}$ = Φ | | Φ-N(CH$_3$)$_2$ |
| 4 | S | ClO$_4$ or I | R$_6$ = Φ<br>R$_7$ = H<br>R$_8$ = A<br>R$_9$ = H<br>R$_{10}$ = Φ | | Φ-N(CH$_3$)$_2$ |
| 5 | O | ClO$_4$ or I | R$_6$ = Φ<br>R$_7$ = H<br>R$_8$ = L-A<br>R$_9$ = H<br>R$_{10}$ = Φ | general formula [II]<br>n = 0<br>Z = H | Φ-N(CH$_2$CH$_3$)$_2$ |
| 6 | S | ClO$_4$ or I | R$_6$ = Φ<br>R$_7$ = H<br>R$_8$ = L-A<br>R$_9$ = H<br>R$_{10}$ = Φ | general formula [II]<br>n = 0<br>Z = H | Φ-N(CH$_2$CH$_3$)$_2$ |
| 7 | O | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | Φ-N(CH$_3$)$_2$ |
| 8 | S | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | Φ-N(CH$_3$)$_2$ |
| 9 | O | ClO$_4$ or I | R$_6$ = Φ<br>R$_7$ = H<br>R$_8$ = L-A<br>R$_9$ = H<br>R$_{10}$ = Φ | general formula [II]<br>n = 1<br>Z = H | Φ-N(CH$_3$)$_2$ |
| 10 | S | ClO$_4$ or | R$_6$ = Φ<br>R$_7$ = H | general formula [II]<br>n = 1 | Φ-N(CH$_3$)$_2$ |

TABLE 2-continued $$\begin{array}{c} R_8 \\ R_9 \\ R_{10} \\ \overset{+}{X} \\ Y^- \end{array} R_7 R_6$$

| Compound No. | X | Y | $R_i$ | L | A |
|---|---|---|---|---|---|
| | | I | $R_8 = L\text{-}A$<br>$R_9 = H$<br>$R_{10} = \Phi$ | $Z = H$ | |
| 11 | O | ClO$_4$<br>or<br>I | $R_6 = \Phi$<br>$R_7 = H$<br>$R_8 = L\text{-}A$<br>$R_9 = H$<br>$R_{10} = \Phi$ | general formula [II]<br>$n = 1$<br>$Z = (-)CH=CH\text{-}\Phi\text{-}N(CH_3)_2$ | $\Phi\text{-}N(CH_3)_2$ |
| 12 | S | ClO$_4$<br>or<br>I | $R_6 = \Phi$<br>$R_7 = H$<br>$R_8 = L\text{-}A$<br>$R_9 = H$<br>$R_{10} = \Phi$ | general formula [II]<br>$n = 1$<br>$Z = (-)CH=CH\text{-}\Phi\text{-}N(CH_3)_2$ | $\Phi\text{-}N(CH_3)_2$ |
| 13 | O | ClO$_4$<br>or<br>I | $R_6 = \Phi$<br>$R_7 = H$<br>$R_8 = L\text{-}A$<br>$R_9 = H$<br>$R_{10} = \Phi$ | general formula [III]<br>$n = 1$ | $\Phi\text{-}N(CH_3)_2$ |
| 14 | S | ClO$_4$<br>or<br>I | $R_6 = \Phi$<br>$R_7 = H$<br>$R_8 = L\text{-}A$<br>$R_9 = H$<br>$R_{10} = \Phi$ | general formula [III]<br>$n = 1$ | $\Phi\text{-}N(CH_3)_2$ |
| 15 | O | ClO$_4$<br>or<br>I | $R_6 = \Phi$<br>$R_7 = H$<br>$R_8 = L\text{-}A$<br>$R_9 = H$<br>$R_{10} = \Phi$ | general formula [IV] | $\Phi\text{-}N(CH_2CH_3)_2$ |
| 16 | S | ClO$_4$<br>or<br>I | $R_6 = \Phi$<br>$R_7 = H$<br>$R_8 = L\text{-}A$<br>$R_9 = H$<br>$R_{10} = \Phi$ | general formula [IV] | $\Phi\text{-}N(CH_2CH_3)_2$ |
| 17 | O | ClO$_4$<br>or<br>I | $R_6 = \Phi$<br>$R_7 = H$<br>$R_8 = \Phi$<br>$R_9 = H$<br>$R_{10} = L\text{-}A$ | general formula [IV] | $\Phi\text{-}N(CH_2CH_3)_2$ |
| 18 | S | ClO$_4$<br>or<br>I | $R_6 = \Phi$<br>$R_7 = H$<br>$R_8 = \Phi$<br>$R_9 = H$<br>$R_{10} = L\text{-}A$ | general formula [IV] | $\Phi\text{-}N(CH_2CH_3)_2$ |
| 19 | O | ClO$_4$<br>or<br>I | $R_6 = \Phi$<br>$R_7 = H$<br>$R_8 = \Phi$<br>$R_9 = H$<br>$R_{10} = L\text{-}A$ | general formula [V] | 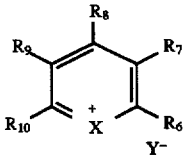 |
| 20 | S | ClO$_4$<br>or<br>I | $R_6 = \Phi$<br>$R_7 = H$<br>$R_8 = \Phi$<br>$R_9 = H$<br>$R_{10} = L\text{-}A$ | general formula [V] | 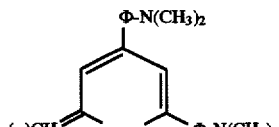 |
| 21 | O | ClO$_4$<br>or<br>I | $R_6 = \Phi$<br>$R_7 = H$<br>$R_8 = \Phi$<br>$R_9 = H$<br>$R_{10} = L\text{-}A$ | general formula [V] | 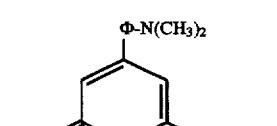 |

TABLE 2-continued

| Compound No. | X | Y | $R_i$ | L | A |
|---|---|---|---|---|---|
| 22 | O | ClO$_4$ or I | $R_6 = \Phi$<br>$R_7 = H$<br>$R_8 = \Phi$<br>$R_9 = H$<br>$R_{10} = L$-A | general formula [VI] | |
| 23 | S | ClO$_4$ or I | $R_6 = \Phi$<br>$R_7 = H$<br>$R_8 = \Phi$<br>$R_9 = H$<br>$R_{10} = L$-A | general formula [VI] | |
| 24 | O | ClO$_4$ or I | $R_6 = \Phi$<br>$R_7 = H$<br>$R_8 = \Phi$<br>$R_9 = H$<br>$R_{10} = L$-A | general formula [VI] | |
| 25 | O | ClO$_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | |
| 26 | S | ClO$_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | |
| 27 | O | ClO$_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | |
| 28 | S | ClO$_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | |
| 29 | O | ClO$_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | |

TABLE 2-continued

| Compound No. | X | Y | $R_i$ | L | A |
|---|---|---|---|---|---|
| 30 | O | ClO₄ or I | $R_6 = \Phi$<br>$R_7 = H$<br>$R_8 = L-A$<br>$R_9 = H$<br>$R_{10} = \Phi$ | general formula [II]<br>n = 0<br>Z = H | (–)CH= [pyrylium ring with O, bearing two $\Phi$-N(CH$_3$)$_2$ groups] |
| 31 | S | ClO₄ or I | $R_6 = \Phi$<br>$R_7 = H$<br>$R_8 = L-A$<br>$R_9 = H$<br>$R_{10} = \Phi$ | general formula [II]<br>n = 0<br>Z = H | (–)CH= [thiopyrylium ring with S, bearing two $\Phi$-N(CH$_3$)$_2$ groups] |
| 32 | O | ClO₄ or I | $R_6 = \Phi$<br>$R_7 = H$<br>$R_8 = L-A$<br>$R_9 = H$<br>$R_{10} = \Phi$ | general formula [II]<br>n = 0<br>Z = H | (–)CH= [thiopyrylium ring with S, bearing two $\Phi$-N(CH$_3$)$_2$ groups] |
| 33 | O or S | ClO₄ or I | $R_6 = \Phi$-N(CH$_3$)$_2$<br>$R_7 = H$<br>$R_8 = A$<br>$R_9 = H$<br>$R_{10} = \Phi$-N(CH$_3$)$_2$ | | $\Phi$-N(CH$_3$)$_2$ |
| 34 | O or S | ClO₄ or I | $R_6 = \Phi$-N(CH$_3$)$_2$<br>$R_7 = H$<br>$R_8 = A$<br>$R_9 = H$<br>$R_{10} = \Phi$-N(CH$_3$)$_2$ | | CH$_3$ |
| 35 | O or S | ClO₄ or I | $R_6 = \Phi$-N(CH$_3$)$_2$<br>$R_7 = H$<br>$R_8 = A$<br>$R_9 = H$<br>$R_{10} = \Phi$-N(CH$_3$)$_2$ | | $\Phi$-COOH |
| 36 | O or S | ClO₄ or I | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | general formula [II]<br>n = 0<br>Z = H | $\Phi$-N(CH$_3$)$_2$ |
| 37 | O or S | ClO₄ or I | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | general formula [II]<br>n = 1<br>Z = H | $\Phi$-N(CH$_3$)$_2$ |
| 38 | O or S | ClO₄ or I | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | general formula [III]<br>n = 1 | $\Phi$-N(CH$_3$)$_2$ |
| 39 | O or S | ClO₄ or I | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | general formula [IV] | $\Phi$-N(CH$_3$)$_2$ |
| 40 | O or S | ClO₄ or I | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | general formula [II]<br>n = 0<br>Z = H | $\Phi$-COOH |
| 41 | O | ClO₄ | $R_6 = \Phi$-N(CH$_3$)$_2$ | general formula [II] | $\Phi$-COOH |

TABLE 2-continued

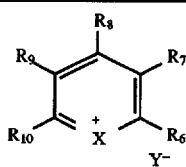

| Compound No. | X | Y | $R_i$ | L | A |
|---|---|---|---|---|---|
| | or S | or I | $R_7 = H$<br>$R_8 = L-A$<br>$R_9 = H$<br>$R_{10} = \Phi-N(CH_3)_2$ | $n = 1$<br>$Z = H$ | |
| 42 | O or S | ClO$_4$ or I | $R_6 = \Phi-N(CH_3)_2$<br>$R_7 = H$<br>$R_8 = L-A$<br>$R_9 = H$<br>$R_{10} = \Phi-N(CH_3)_2$ | general formula [III]<br>$n = 1$ | $\Phi$-COOH |
| 43 | O or S | ClO$_4$ or I | $R_6 = \Phi-N(CH_3)_2$<br>$R_7 = H$<br>$R_8 = L-A$<br>$R_9 = H$<br>$R_{10} = \Phi-N(CH_3)_2$ | general formula [IV] | $\Phi$-COOH |
| 44 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [II]<br>$n = 0$<br>$Z = H$ | $\Phi$-N(CH$_3$)$_2$ |
| 45 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [II]<br>$n = 1$<br>$Z = H$ | $\Phi$-N(CH$_3$)$_2$ |
| 46 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [III]<br>$n = 1$ | $\Phi$-N(CH$_3$)$_2$ |
| 47 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [IV] | $\Phi$-N(CH$_3$)$_2$ |
| 48 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [II]<br>$n = 0$<br>$Z = H$ | $\Phi$-COOH |
| 49 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [II]<br>$n = 1$<br>$Z = H$ | $\Phi$-COOH |
| 50 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [III]<br>$n = 1$ | $\Phi$-COOH |
| 51 | O or S | ClO$_4$ or I | $R_6 = L-A$<br>$R_7 = H$<br>$R_8 = \Phi-N(CH_3)_2$<br>$R_9 = H$<br>$R_{10} = \Phi-N(CH_3)_2$ | general formula [IV] | $\Phi$-COOH |
| 52 | O or S | ClO$_4$ or I | $R_6 = A$<br>$R_7 = H$<br>$R_8 = \Phi-N(CH_3)_2$<br>$R_9 = H$<br>$R_{10} = \Phi-N(CH_3)_2$ | | —COOH |
| 53 | O or S | ClO$_4$ or I | $R_6 = A$<br>$R_7 = H$<br>$R_8 = \Phi-N(CH_3)_2$<br>$R_9 = H$<br>$R_{10} = \Phi-N(CH_3)_2$ | | $\Phi$-COOH |
| 54 | O or S | ClO$_4$ or I | $R_6 = \Phi$<br>$R_7 = H$<br>$R_8 = \Phi-N(CH_3)_2$ | | |

TABLE 2-continued

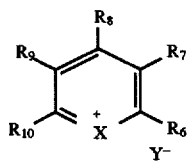

| Compound No. | X | Y | R$_i$ | L | A |
|---|---|---|---|---|---|
| 55 | O or S | ClO$_4$ or I | R$_9$ = H<br>R$_{10}$ = Φ-N(CH$_3$)$_2$<br>R$_6$ = Φ-N(CH$_3$)$_2$<br>R$_7$ = H<br>R$_8$ = Φ<br>R$_9$ = H<br>R$_{10}$ = Φ-N(CH$_3$)$_2$ | | |

The compounds above were synthesized according to known processes as below. The specific reaction operations were conducted in conventional manner.

Compound 7 was prepared by synthesizing Compound [i] according to the method described by W. Foerst et al. ("New Methods of Preparative Organic Chemistry", Acad. Press (1964)),

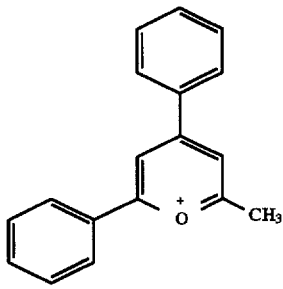

[i]

reacting it with p-N,N-dimethylaminobenzaldehyde (formula shown below):

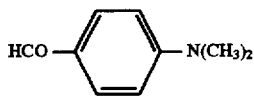

and by reacting the resulting compound with a desired anion.

Compound 17 was prepared by reacting Compound [i] with p-diethylaminostyrylbenzaldehyde (formula shown below):

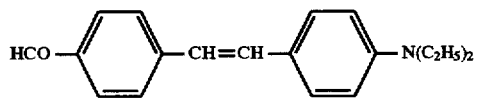

and reaction the resulting product with a desired anion.

Compound [ii] was prepared by reacting Compound [i] with sodium hydrogen sulfide.

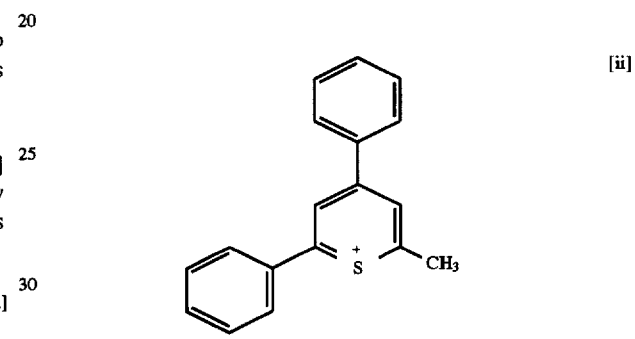

From this Compound [ii], Compounds 8 and 18 were prepared in the same manner as Compounds 7 and 17.

Compound [iii] was synthesized from acetophenone and acetaldehyde according to the method described by R. Wizinger (Helv. Chim. Acta, 39 217 (1956)) through the route shown below:

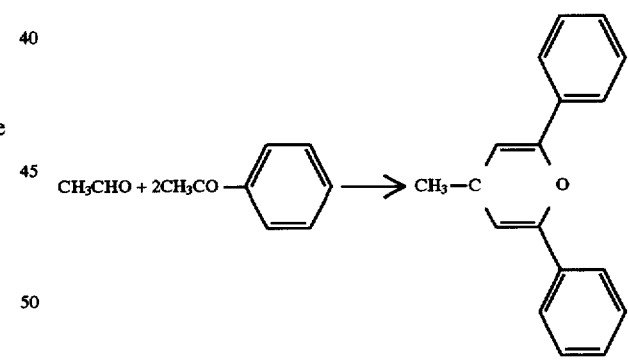

Compound 5 was prepared by reacting Compound [iii] with p-dimethylaminobenzaldehyde, and further reacting the resulting compound with a desired anion.

Compound 15 was prepared in the same manner by using p-diethylaminostyrylbenzaldehyde.

Compound 9 was prepared in the same manner by using p-dimethylaminocinnamaldehyde.

Compound 11 was prepared in the same manner by using the compound below:

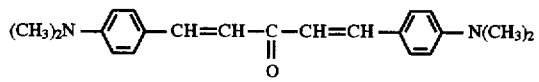

Compound [iv] was obtained by reacting Compound [iii] with sodium hydrogen sulfide:

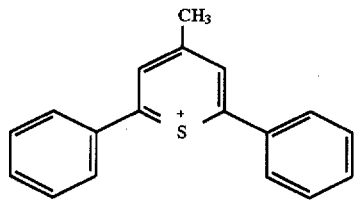

[iv]

Compounds 6, 16, 10, and 12 were prepared respectively in the same manner as Compounds 5, 15, 9, and 11 except that Compound [iv] was used in place of Compound [iii].

The cation portion of Compound 3 was synthesized in the same manner as Compound [iii] except that p-dimethylaminobenzaldehyde was used in place of acetaldehyde as a starting material. Compound 4 was prepared by reacting the above resulting compound with sodium hydrogen sulfide, and further with a desired anion.

Compound [v] was prepared from p-methylbenzaldehyde and acetophenone in the same manner:

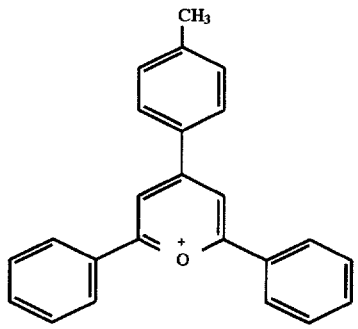

[v]

Compound [vi] was prepared by reacting Compound [v] with sodium hydrogen sulfide:

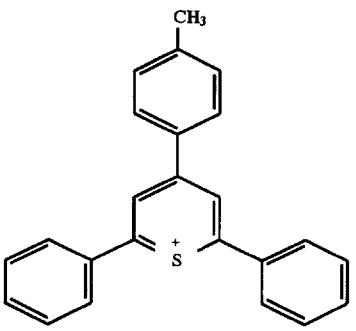

[vi]

Compounds 13 and 14 were prepared respectively by reacting Compound [v] and Compound [vi] respectively with p-dimethylaminobenzaldehyde, and the resulting compound with a desired anion.

Compounds 19, 20, and 21 were prepared respectively by reacting Compound [i] or [ii] with the cation portion of Compound 1 or 2, and the compound of the formula below:

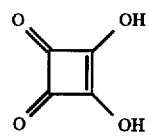

and reacting the product further with a desired anion.

Compounds 22, 23, and 24 were prepared respectively by reacting Compound [i] or [ii] with the cation portion of Compound 1 or 2, and the compound of the formula below:

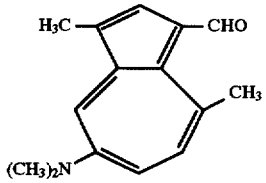

and reacting the product further with a desired anion.

Compounds 25 and 26 were prepared respectively by reacting Compound [i] or [ii] with the compound of the formula below:

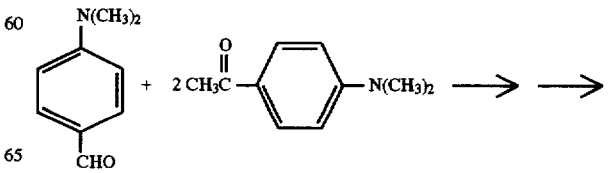

and reacting the product further with a desired anion.

Compounds 27, 28, and 29 were prepared respectively by reacting Compound [i] or [ii] with the cation portion of Compound 1 or 2, and ethyl orthoformate [$HC(OC_2H_5)_3$], and reacting the product further with a desired anion.

Compounds 30, 31, and 32 were prepared respectively by reacting Compound [iii] or [iv] with a p-dimethylamino derivative of Compound [iii] or [iv] derived in the same manner as Compound [iii] or [iv], and ethyl orthoformate, and reacting the product further with a desired anion.

Compounds 33 to 55 were synthesized through the processes below.

Synthesis of Compound 33

31
-continued
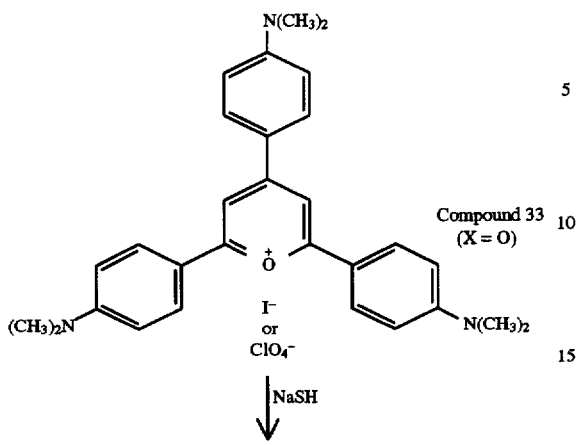
Compound 33 (X = O)
↓ NaSH
Compound 33 (X = S)
Synthesis of Compound 34
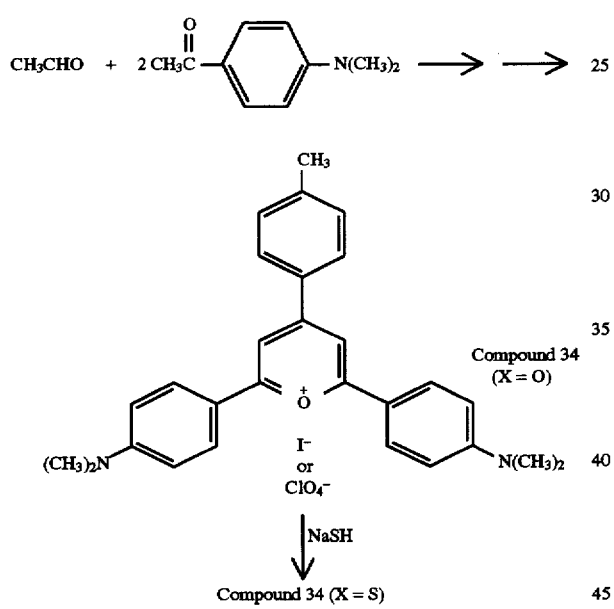
Compound 34 (X = O)
↓ NaSH
Compound 34 (X = S)
Synthesis of Compound 35
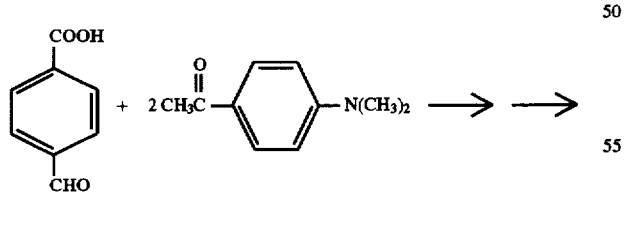
32
-continued
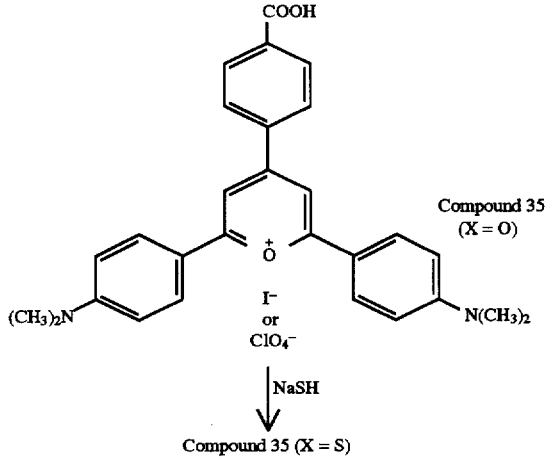
Compound 35 (X = O)
↓ NaSH
Compound 35 (X = S)
Synthesis of Compound 36
Compound 34 (X = O) + 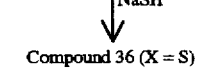
↓
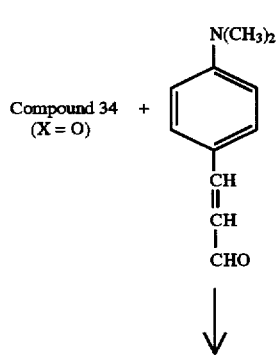
Compound 36 (X = O)
↓ NaSH
Compound 36 (X = S)
Synthesis of Compound 37
Compound 34 (X = O) +
↓

33
-continued

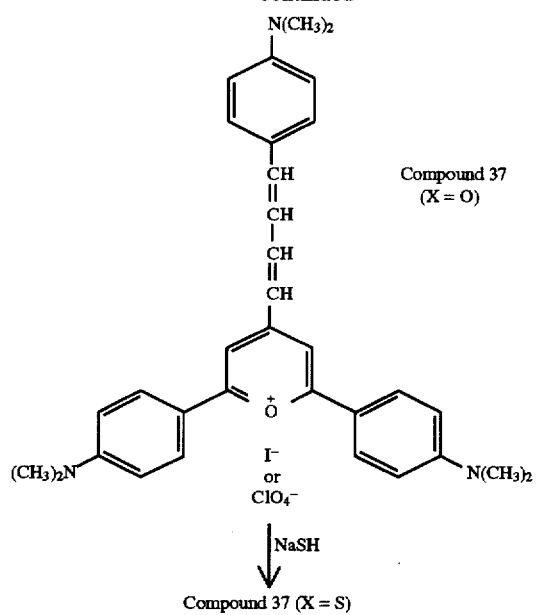

Compound 37 (X = O)

↓ NaSH

Compound 37 (X = S)

Synthesis of Compound 38

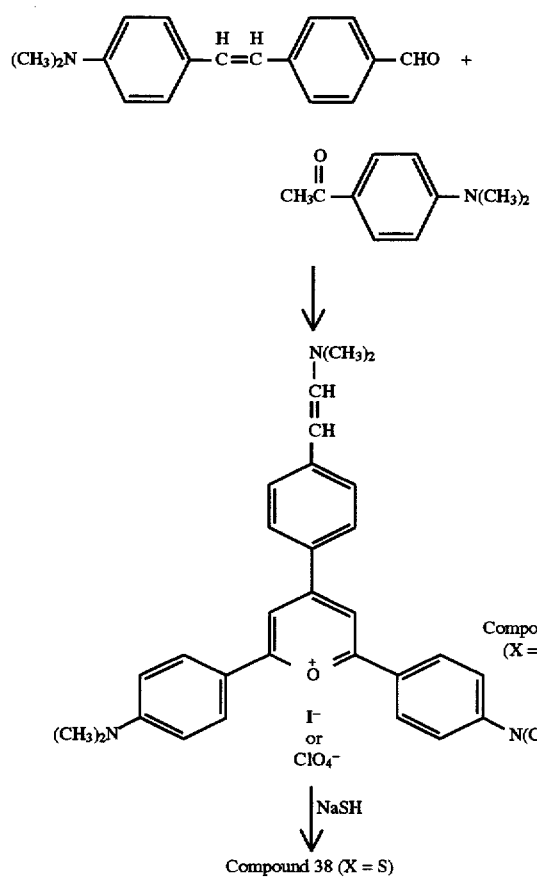

Compound 38 (X = O)

↓ NaSH

Compound 38 (X = S)

34
-continued
Synthesis of Compound 39

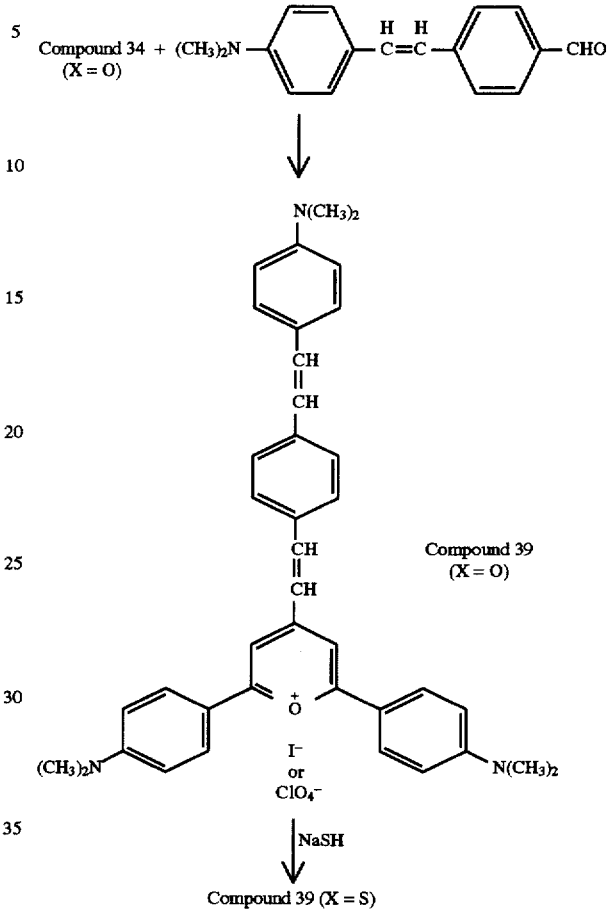

Compound 39 (X = O)

↓ NaSH

Compound 39 (X = S)

Compound 40 was synthesized in the same manner as Compound 36 except for using the compound

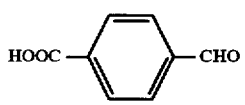

in place of

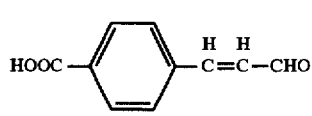

as a starting material.

Compound 41 was synthesized in the same manner as Compound 37 except for using the compound HOOC—⟨benzene⟩—CH=CH—CHO in place of
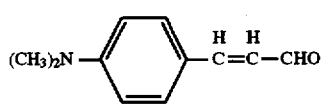
as a starting material.
Compound 42 was synthesized in the same manner as Compound 38 except for using the compound
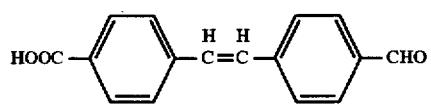
in place of
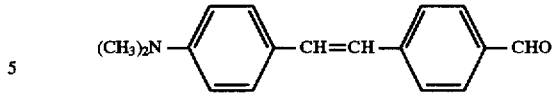
as a starting material.
Compound 43 was synthesized in the same manner as Compound 39 except for using the compound
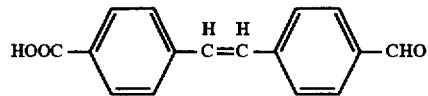
in place of
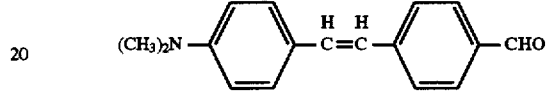
as a starting material.
Synthesis of Compound 44
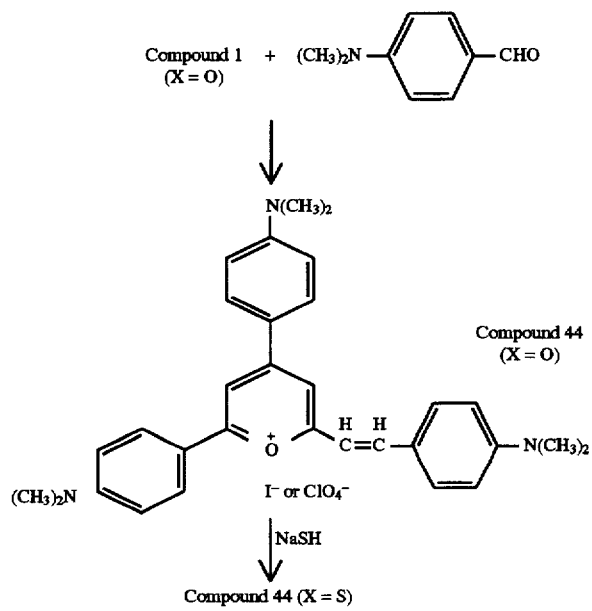
Synthesis of Compound 45
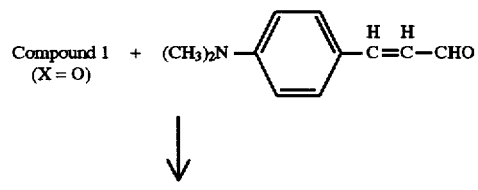

-continued
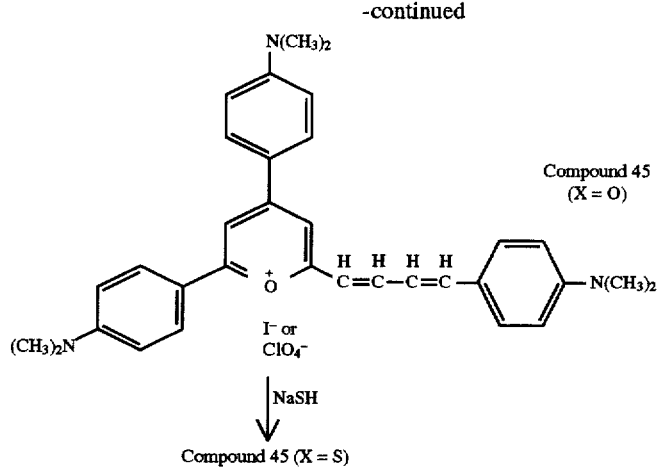
Compound 45 (X = O)
Compound 45 (X = S)
Synthesis of Compound 46
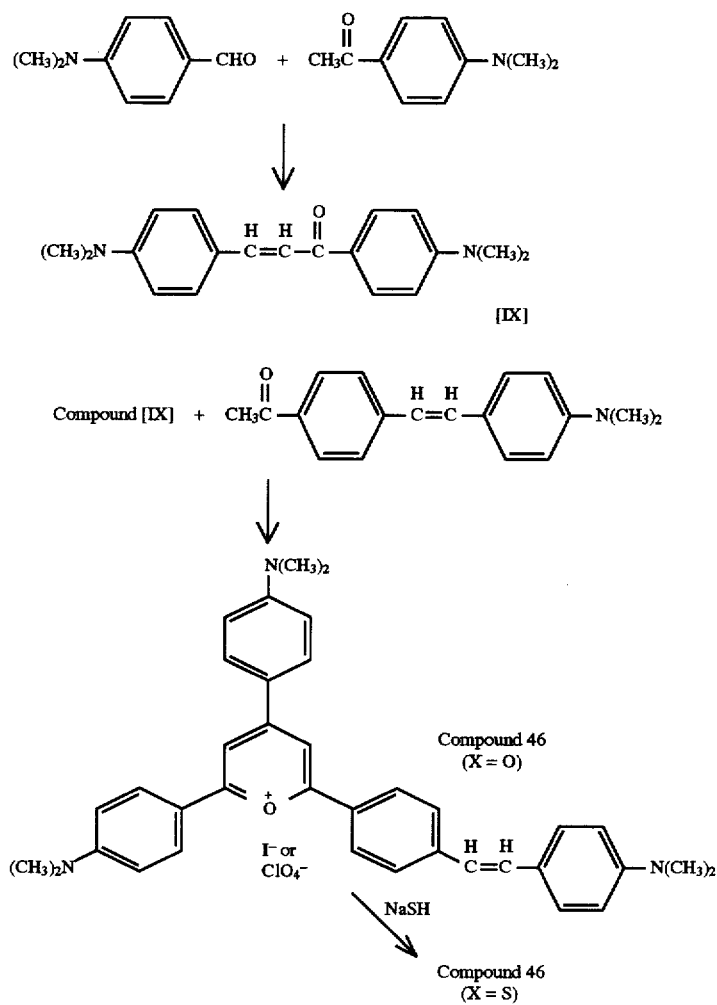
Compound 46 (X = O)
Compound 46 (X = S)

-continued
Synthesis of Compound 47

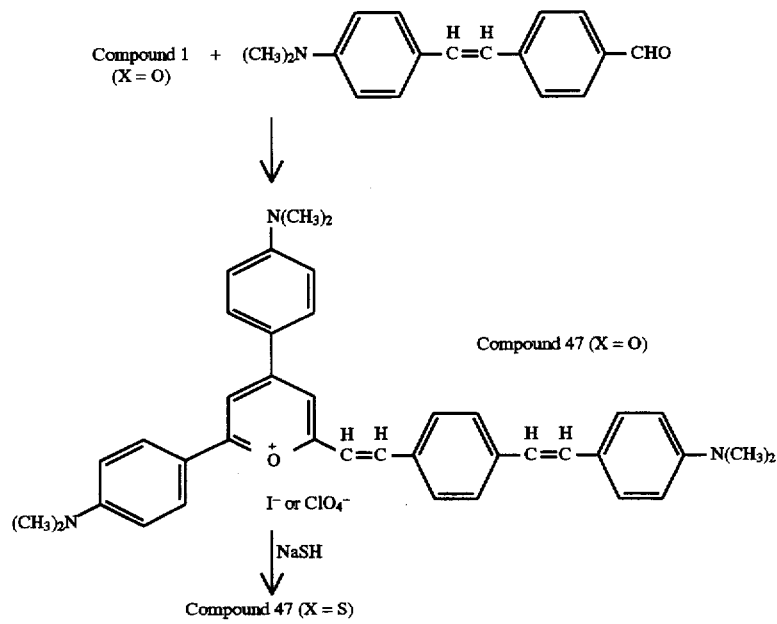

Compound 48 was synthesized in the same manner as Compound 44 except for using the compound

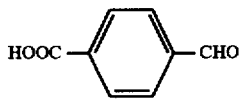

in place of

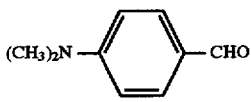

as a starting material.

Compound 49 was synthesized in the same manner as Compound 45 except for using the compound

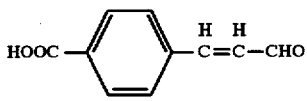

in place of

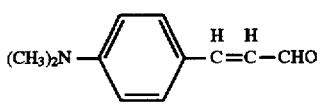

as a starting material.

Compound 50 was synthesized in the same manner as Compound 46 except for using the compound

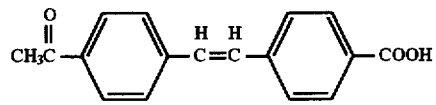

in place of

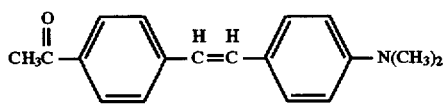

as a starting material.

Compound 51 was synthesized in the same manner as Compound 47 except for using the compound

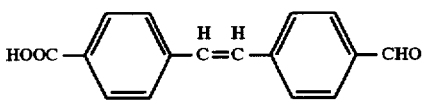

in place of

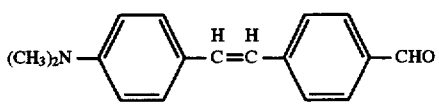

as a starting material.

Synthesis of Compound 52

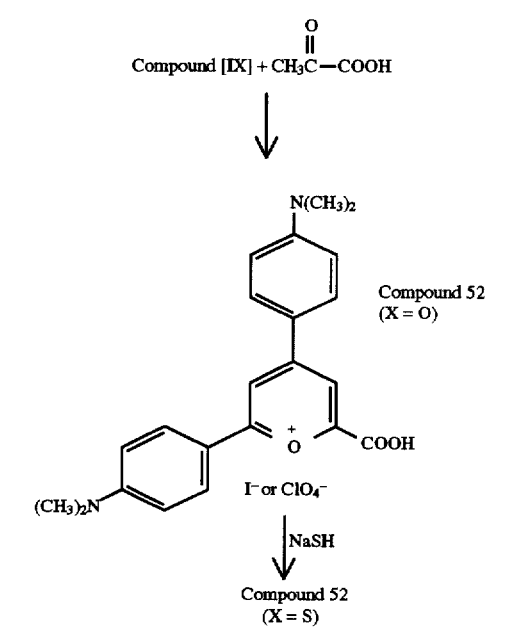

Synthesis of Compound 53

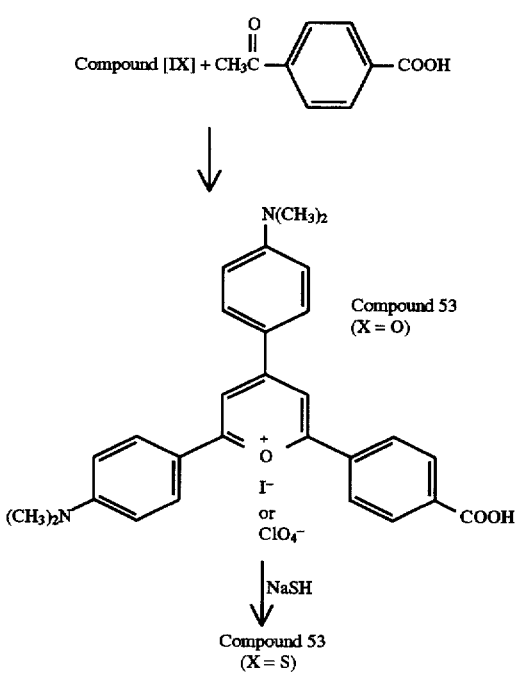

Synthesis of Compound 54

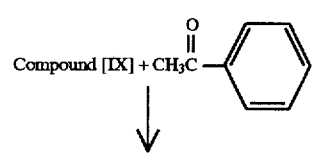

-continued

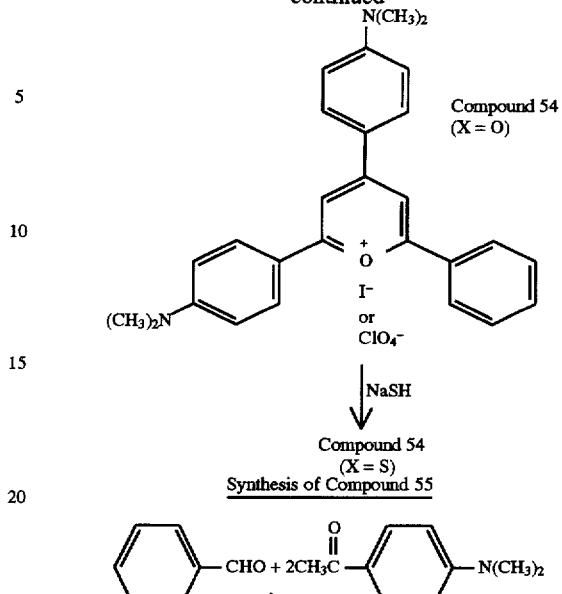

Synthesis of Compound 55

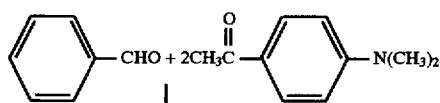

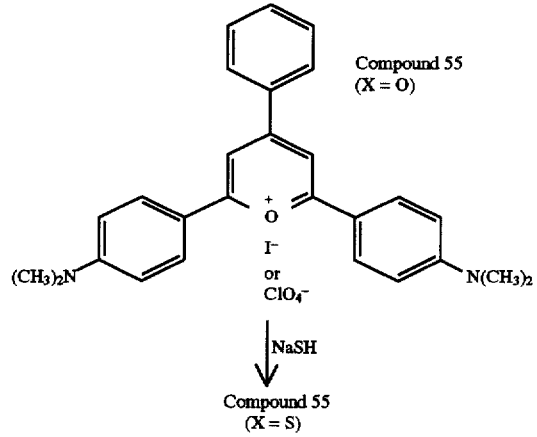

Reference Example 4

Compound 1 obtained in Reference Example 1 was dissolved in acetonitrile to make a stock solution, to which a phosphate buffer was added to the final concentration of 10 mM, followed by dilution with water containing 10% acetonitrile to the final concentration of Compound 1 of $3 \times 10^{-5}$M. This solution is referred to as "Sample I". The absorption spectrum of Sample I was measured with a spectrophotometer in a conventional manner.

Salmon sperm DNA (made by SiGma Co.) was dissolved in a TE buffer solution (10 mM Tris—1 mM EDTA), and was purified by phenol extraction. The purified DNA was further digested with restriction enzyme EcoRI for easy handling. An aliquot of this DNA solution was mixed with the stock solution of Compound I to give a DNA concentration of 50 μg/ml and a Compound 1 concentration of $3 \times 10^{-5}$M. This solution containing 10% acetonitrile is referred to as "Sample II". The absorption spectrum of Sample II was measured with a spectrophotometer in a conventional manner. In Sample II, the absorption peak of Compound 1 shifted by 20 to 30 nm to longer wavelength owing to its interaction with DNA, which is typical for an intercalator.

When fluorescence spectrum of Sample I and Sample II were taken in a conventional manner, sample I showed a trace fluorescence peak at about 650 nm by excitation at 550 nm, whereas Sample II containing DNA showed a strong fluorescence peak at about 650 nm with an intensity of about 100 times that of Sample I at the same excitation wavelength. This shows that Compound 1 is a powerful intercalator.

Solutions were prepared which contain Compound 1 at a concentration of $5 \times 10^{-6}$ M and DNA at various concentrations by using the above-prepared DNA solution and the above-prepared 10 mM phosphate buffer solution containing compound 1 and 10% acetonitrile. The fluorescence intensities of the solutions were measured in a conventional manner to determine the relation to the DNA concentration. The fluorescence intensity increased in proportion to the DNA concentration, the maximum intensity being about 400 times the value in the absence of DNA. The excitation light was emitted from a xenon lamp through a low-cut filter of 480 nm to eliminate ultraviolet light. Further, the compounds shown in Table 2 were subjected to fluorescence intensity measurement in the same manner as above. Typical examples are shown in Table 3.

TABLE 3

| Compound No. | Maximum absorption wavelength | | Fluorescence intensity | |
|---|---|---|---|---|
| | Absence of DNA | Presence of DNA | $\lambda_{em}$ | Increase |
| 1 | 540 nm | 560 nm | 650 nm | 100-fold |
| 2 | 580 nm | 620 nm | 700 nm | 60-fold |
| 3 | 535 nm | 570 nm | 640 nm | 13.6-fold |
| 4 | 575 nm | 610 nm | 705 nm | 10-fold |
| 6 | 660 nm | 690 nm | 800 nm | 7-fold |
| 8 | 650 nm | 670 nm | weak | — |
| 9 | 660 nm | 720 nm | 750 nm | 16-fold |
| 11 | 625 nm | 660 nm | 735 nm | 10-fold |
| 15 | 670 nm | 680 nm | 820 nm | 5-fold |
| 16 | 690 nm | 720 nm | 825 nm | 5-fold |
| 17 | 690 nm | 720 nm | weak | — |

Example 1

[Determination of nucleic acid with 2,4-bis(4-N,N-dimethylaminophenyl)-6-methylpyrylium salt]

PCR was carried out on 16S ribosomal RNA gene (hereinafter referred to as 16S rRNA gene) of *Pseudomonas aeruginosa* as the target, and the amplification product was detected by use of 2,4-bis(4-N,N-dimethylaminophenyl)-6-methylpyrylium salt.

Firstly, the entire DNA of *P. aeruginosa* was prepared as follows. After overnight incubation in a 2×YT culture medium, the cells of 2 ml culture were collected by centrifugation. The collected cells were suspended in 0.5 ml of 0.1M phosphate buffer solution (pH: 8.0), to which 0.05 ml of 10% SDS solution was added. The suspension was mixed well, and was kept standing at 70° C. for one hour. Then the suspension was vortexed to cause complete cell lysis. To this lysate, an equal amount of phenol-chloroform was added, and mixed. Then the mixture was centrifuged, and the upper layer was collected. Thereto ethanol of twice volume was added to recover DNA as precipitate. The DNA was dissolved in 100 μl of TE buffer (pH: 8.0). This DNA was used as the template DNA.

Two primers were used for PCR.
Primer 1: 5' AGAGTTTGATCATGGCTCAG 3' (sequence No. 1)
Primer 2: 5' AACCCAACATCTCACGACAC 3' (sequence No. 2)

These primers were synthesized by means of DNA Synthesizer 381A (made by ABI Co.). The reagents and the techniques for the synthesis are based on the protocol of ABI Co.

PCR was conducted with the template DNA and the primers under the following conditions:
[PCR conditions]
Composition of reaction solution (total volume: 50 μ):

| | |
|---|---|
| 10× buffer*: | 5 μl |
| dNTPs: | 5 μl |
| Primers 1 and 2: | 10 pmol respectively |
| Taq DNA polymerase: | 0.5 unit |
| Template DNA: | 500 pg, 100 pg, 10 pg, 1 pg, 100 fg, or 10 fg |

*(100 mM tris-HCl (pH 9.0), 500 mM KCl, 1% Triton X-100, 25 mM $MgCL_2$)

The components were mixed and thereto sterilized water was added to the total volume of 50 μl. The mixture was allowed to react in a Thin-Walled Gene Amp tube (entire volume: 0.5 ml, made by Takara Shuzo Co., Ltd.). Separately, as the blank, a sample was prepared in the same manner as above except that the template DNA was not added. The required amount of the 10×buffer (100 mM tris-HCl(pH 9.0), 500 mM KCl, 1% Triton X-100, 25 mM $MgCL_2$) and the dNTPs were supplied with the polymerase. Reaction cycle:

Pre-incubation at 92° C. for 5 minutes, 30 cycles of 92° C. for 45 seconds/55° C. for 60 seconds/and 72° C. for 90 seconds, Final incubation at 72° C. for 5 minutes followed by slow cooling down to 5° C. for annealing.

Figure 2:
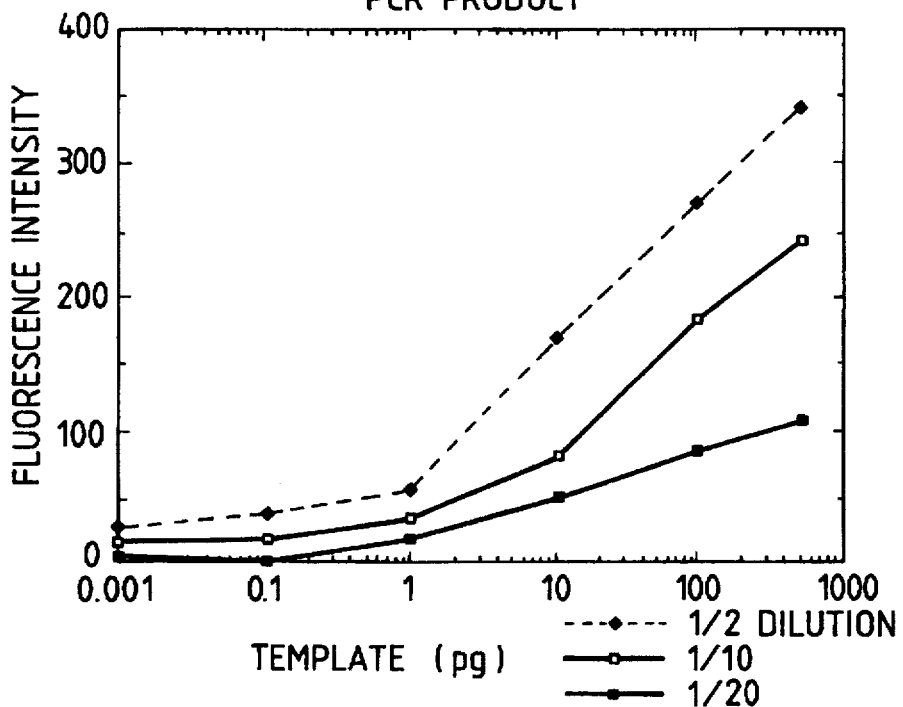
FIG. 2 shows the relation between the fluorescence intensity and the amount of template DNA in Example 1.

The PCR apparatus employed was Gene PCR System 9600 made by Perkin-Elmer Inc. The amplification product was detected as follows: After the reaction, respective samples are diluted 2-fold, 10-fold, and 20-fold with TE buffer (10 mM Tris-HCl (pH: 8.0)–1 mM EDTA), to the final volume of 50 μl on a 96-well microtiter plate (Falcon Assay Plate 3911 (U-bottomed well) made by Becton-Dickinson Co.) (See FIG. 1). To each of the wells, was added 1 μl of 150 μg/ml 2,4-bis(4-N,N-dimethylaminophenyl)-6-methylpyrylium iodide solution in acetonitrile. The contents of the wells were mixed well by pipetting. The microplate was set on a Millipore Fluorescence Apparatus (CytoFluor 2350), and using the excitation filter to pass the light of wavelength 590 nm and the emission filter to detect the light of wavelength 645 nm, the fluorescence under the excitation light irradiation was measured. FIG. 2 shows the fluorescence intensity at 645 nm of the respective dilutions as a function of the amount of the template DNA in the reaction. No fluorescence was observed with the blank sample. As shown in FIG. 2, the fluorescence intensity increases as the amount of the template DNA increases, showing the possibility of quantitative determination of template DNA with fluorescence intensity. At the template DNA levels of 100 fg and 10 fg, no PCR amplification product was detected.

The same operation was conducted, but instead of detection with 2,4-bis(4-N,N-dimethylamtnophenyl)-6-methylpyrylium salt to the reaction solution in each of the well, a 5 μl aliquot of the respective reaction solutions were taken out and subjected to agarose gel electrophoresis. The gel was stained with ethidium bromide (hereinafter referred to as EB), and the amount of the PCR amplification product was estimated from the fluorescence density of the band. As a result, a distinct band was observed at the template DNA levels of 500 pg, 100 pg, and 10 pg; a weak band was observed at the level of 1 pg; and no PCR amplification product was observed at the levels of 100 fg and 10 fg of template DNA used. At the level of 500 pg, the fluorescence intensity was saturated, giving intensity nearly equal to that of 100 pg template DNA. On the gel, in addition to the band of the PCR amplification product, a fluorescent zone was observed at a lower molecular weight region, which is assumed to come from higher-ordered product formed between the primers.

Comparative Example 1

[Detection of PCR Amplification Product with EB]

The same operation was conducted as in Example 1 except that EB was used in place of 2,4-bis(4-N,N-dimethylaminophenyl)-6-methylpyrylium salt with the following operation conditions. To each of the wells, was added 1 µl of 250 µg/ml EB solution, and mixed well by pipetting. The mixture was left standing at room temperature for 5 minutes. The fluorescence intensities were measured by means of Millipore Fluorescence Apparatus with a 485 nm-light transmitting excitation filter and a 620 nm-light transmitting emission filter. Consequently, red fluorescence was observed at all the wells including control wells. Moreover, no difference of the fluorescence intensity was observed between the sample wells containing the template DNA and the wells not containing template DNA (control wells). Therefore, the quantitative determination was impossible. This was attributed to the presence of higher-order structured matter formed from primers in the sample and blank wells.

Comparative Example 2

[Detection of PCR Amplification Product Employing YOYO-1]

Figure 3:
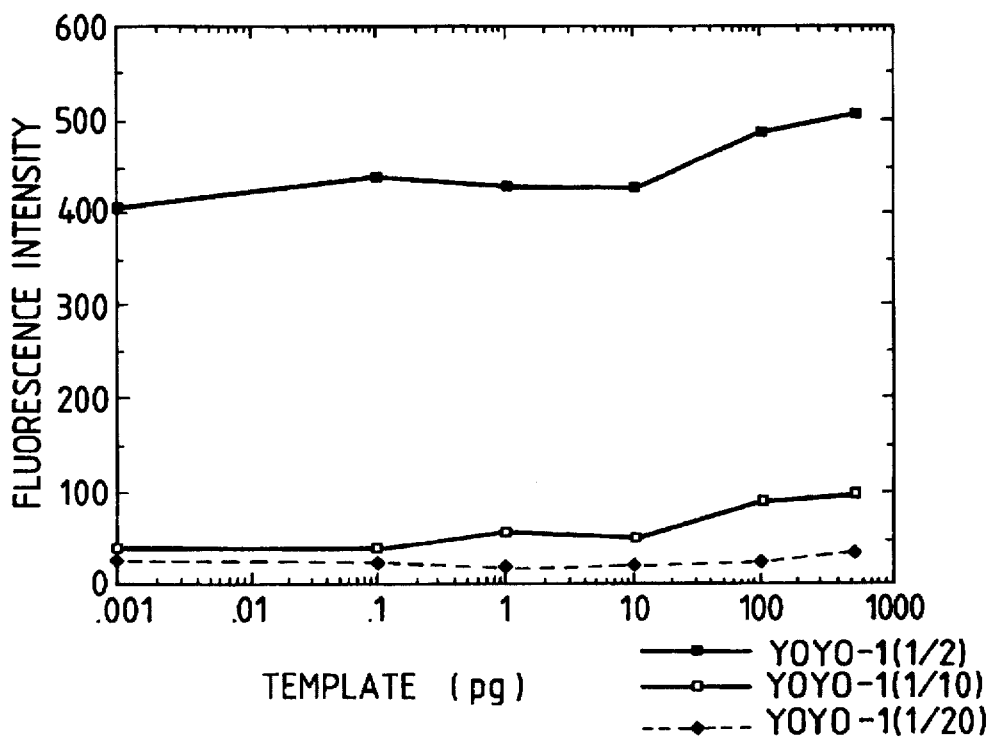
FIG. 3 shows the relation between the fluorescence intensity and the amount of template DNA in Comparative Example 2.

The same operation was conducted as in Example 1 except that YOYO-1 (made by Molecular Probe Co.) was used in place of 2,4-bis(4-N,N-dimethylaminophenyl)-6-methylpyrylium salt with the following operation conditions. The YOYO-1 solution was prepared by diluting 1 mM stock solution 120-fold, and 1 µl of the diluted YOYO-1 solution was added to each of the wells, and mixed well by pipetting. The mixture was left standing at room temperature for 5 minutes. The fluorescence intensities were measured by means of Millipore Fluorescence Apparatus with a 485 nm-light transmitting excitation filter and a 530 nm-light transmitting emission filter. FIG. 3 shows the results. As shown in FIG. 3, the fluorescence intensity increased in proportion to the amount of the template DNA, but the increase rate is low. Moreover, the blank wells also produced fluorescence at approximately the same intensity level as those containing the template DNA. The fluorescence of the blank is probably due to the higher-order structured product formed from the primers. Accordingly, in the quantitative determination with this dye, quantitation is not satisfactory because of the small difference in the fluorescence intensity between the reaction mixture and the blank mixture and the low increase rate of the fluorescence intensity in proportion to the amount of the template DNA.

From the results of Example 1 and Comparative Examples 1 and 2, the quantitative determination can be conducted precisely by utilizing the fluorescence 2,4-bis(4-N,N-dimethylaminophenyl-6-methyl)pyrylium iodide not influenced by the higher-order structured product formed from the primers. This result is well consistent with the result of EB staining of agarose gel electrophoresis of the reaction solutions in Example 1. In EB staining of the agarose gel, however, the fluorescence saturated at the template DNA levels of 500 pg and 100 pg, apparently showing the presence of the same quantity of the amplification products of the template DNA levels of 100 pg or higher. On the other hand, in the detection with 2,4-bis(4-N,N-dimethylaminophenyl)-6-methylpyrylium salt, the fluorescence intensity does not saturate even at the levels in which EB fluorescence saturates, thereby, quantitative determination being practicable.

Example 2

[Measurement of Bacterial Cell Number by PCR Employing a Microplate]

An overnight culture (2×YT medium) of $E.$ $coli$ JM109 strain was added to soil. From the soil, DNA was extracted in a conventional manner, and subjected to PCR targeting 16S rRNA gene of $E.$ $coli$ as the template, to determine the number of bacterial cells by PCR-MPN method.

$E.$ $coli$ was added to the soil to give cell numbers per gram of soil of about 107, about 106, about 105, and about 104 (corresponding to Samples A, B, C, and D in FIG. 4, respectively), and the soil samples were stirred. One gram of the soil sample containing $E.$ $coli$ was respectively suspended in 0.5 ml of 1M phosphate buffer solution (pH 8.0). To the suspension, 0.05 ml of 10% SDS solution was added. The mixture, after being sufficiently stirred, was left standing at 70° C. for one hour. The suspension was mixed with a vortex mixer for complete cell lysis. To the lysate, an equal amount of a phenol-chloroform mixture was mixed. After centrifugation, the upper layer was collected. Thereto, twice the amount of ethanol was added to recover DNA as the precipitate. This precipitate was dissolved in 100 µl of a TE buffer solution (pH 8.0) to form a template DNA solution for PCR.

The following two PCR primers selective for 16S rRNA gene of $E.$ $coli$ were employed.

Primer 1: 5' AGAGTTTGATCCTGGCTCAG 3' (Sequence No. 3)

Primer 2: 5' AACCCAACATCTCACGACAC 3' (Sequence No. 4)

These primers were synthesized by means of Synthesizer 381A made by ABI Co. The reagents and the techniques for the synthesis were based on the protocol of ABI Co.

Figure 4:
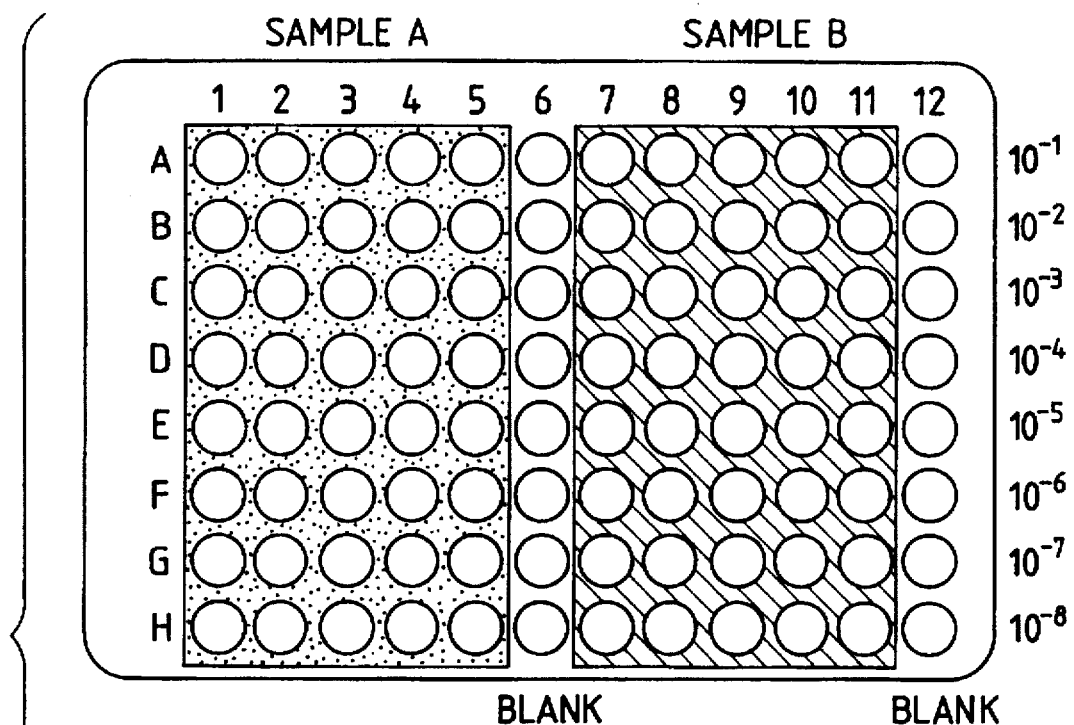
FIG. 4 illustrates an arrangement of samples prepared in Example 2 on a microplate.
Figure 4:
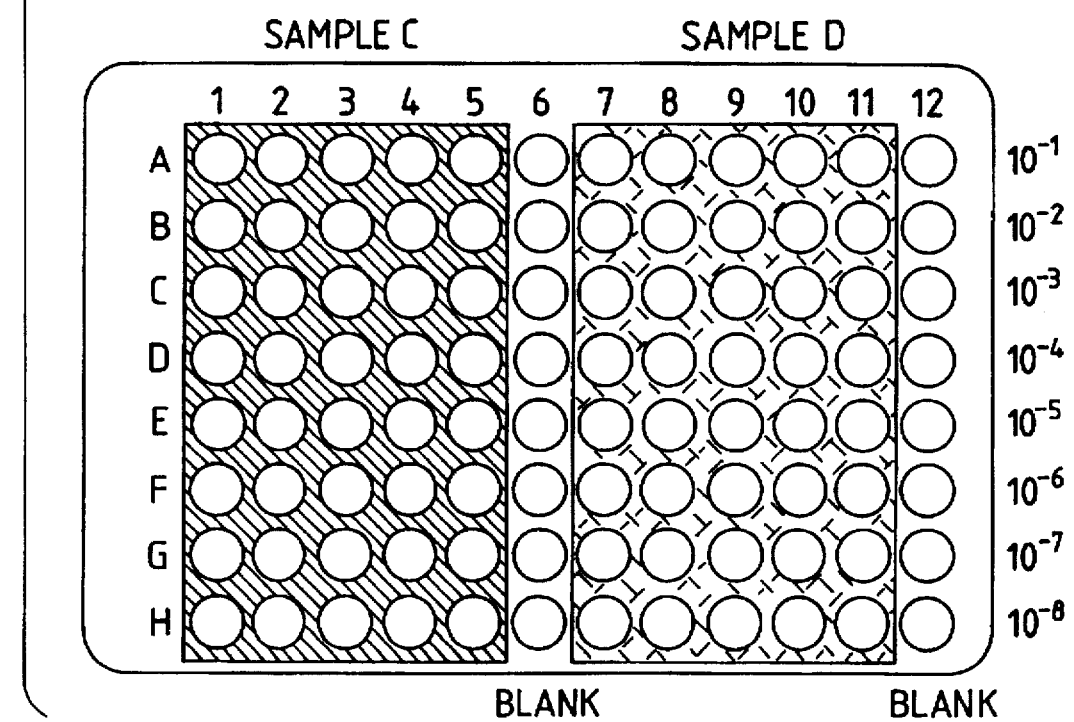

PCR was conducted with the extracted DNA as the template and the primers under the same conditions as in Example 1. The PCR was conducted in the wells (U-bottomed) of a 96-well microtiter plate (Falcon assay plate 3911 made by Becton-Dickinson Inc.). Each well of the microplate contains preliminarily applied and dried 1 µl of a solution of 2,4-bis(N,N-dimethylamino-phenyl)-6-methylpyrylium iodide in acetonitrile of the same concentration as in Example 1. Starting from the DNA solution (the extracted DNA solved in 100 µl), eight successive 10-fold dilutions of the template DNA ($10^{-1}$ to $10^{-8}$) were prepared and each dilution (1 µl) was distributed in five wells in one line as shown in FIG. 4 for the PCR reaction. The PCR reaction apparatus was Model PTC-100-96 made by MJ Research Inc.

Figure 5:
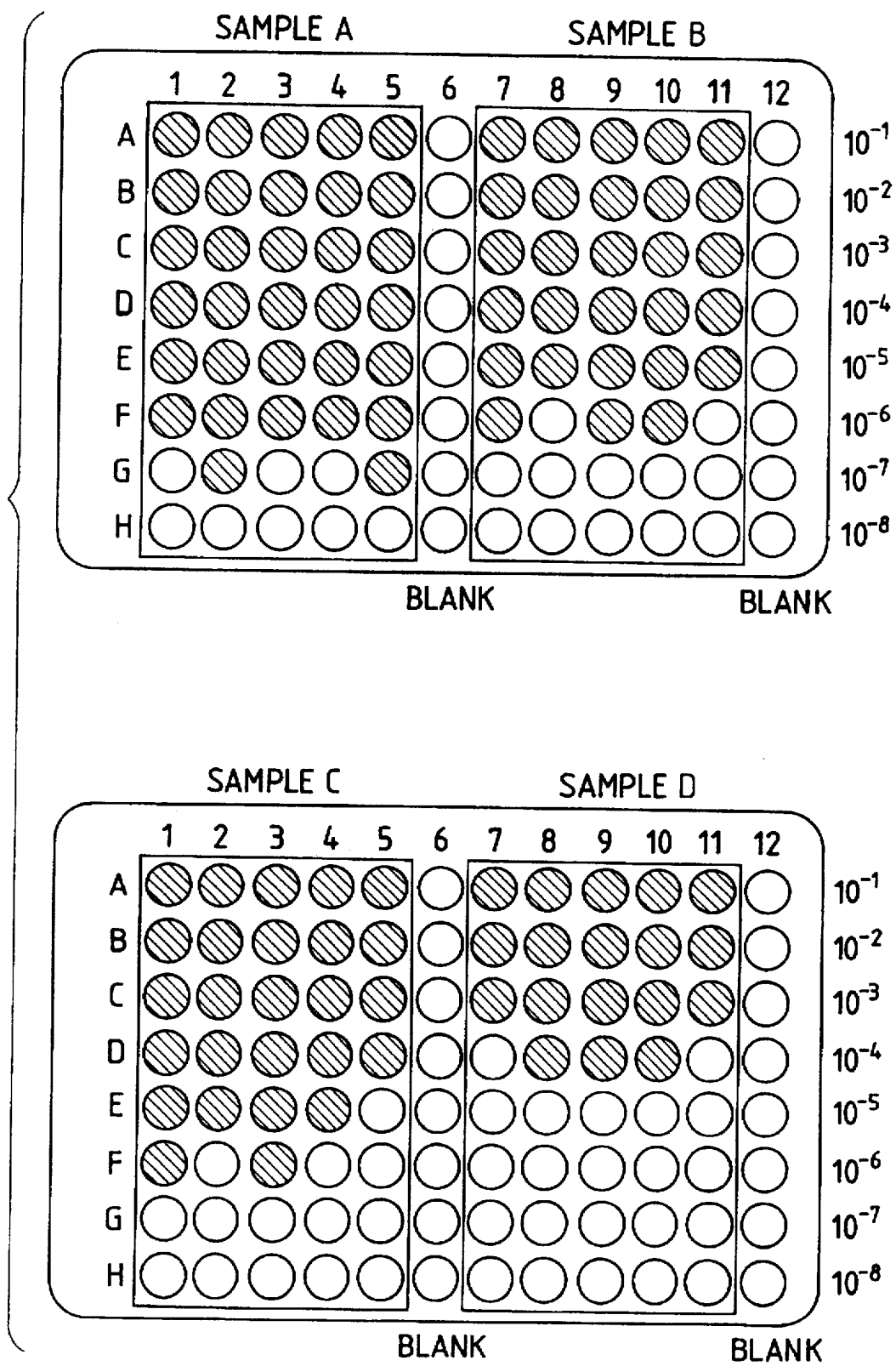
FIG. 5 shows the formation of a PCR amplification product in the respective samples on the microplate in Example 2. The shadowing shows the wells of which fluorescence intensity was twice or more of the blank.

After the PCR reaction, 5 µl of acetonitrile was added to each of the wells on the microplate. Each mixture was agitated sufficiently, and was left standing for 5 minutes. Then the microplate was set on a Millipore Fluorescence Apparatus (CytoFluor 2350), and the fluorescence was measured with the same filters employed in Example 1. FIG. 5 shows the results. The wells producing fluorescence of twice or more that of the blank wells were regarded to contain a PCR amplification product (shadowed wells in FIG. 5). From the results, the numbers of $E.\ coli$ in the respective soil samples were estimated to be $4.9 \times 10^6$, $7.9 \times 10^5$, $2.2 \times 10^5$, and $7.9 \times 10^3$ by reference to the table for MPN.

Comparative Example 3

Figure 6:
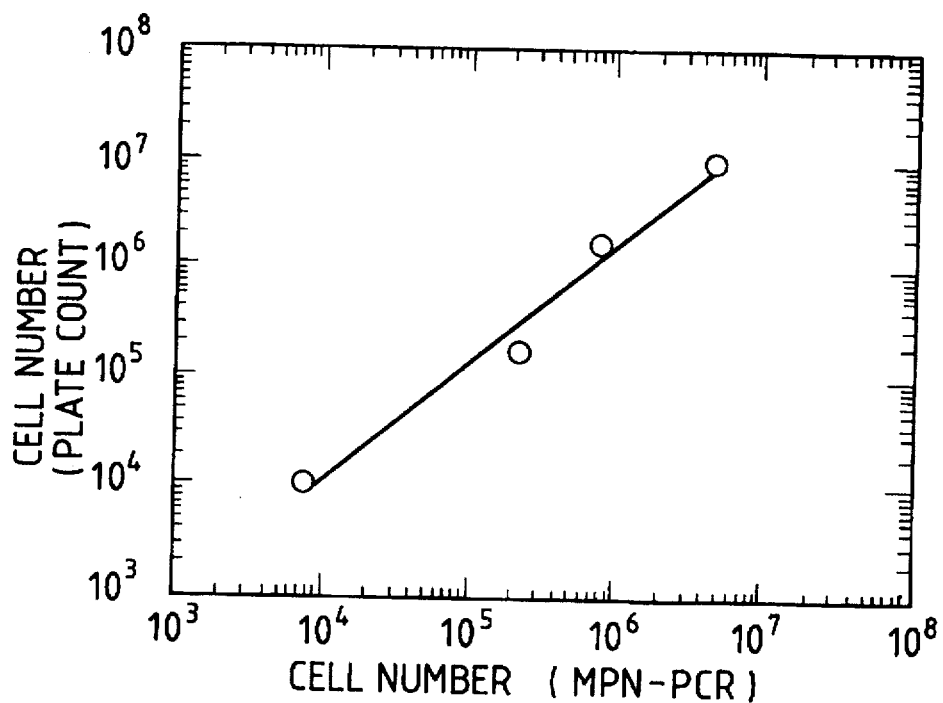
FIG. 6 shows correlation between the cell numbers obtained in Example 2 and those obtained in Comparative Example 3.

The numbers of $E.\ coli$ cells in the same soil samples prepared in Example 2 were measured by plate count method in which a predetermined amount of the sample was inoculated in an $E\ coli$ culture plate and the number of colonies were measured as the viable cell number. The results agreed well with the results obtained in Example 2 as shown in FIG. 6.

From the results of Example 2 and Comparative Example 3, the PCR method of the present invention enables measurement of the number of the cells with simple operations giving well agreed results with that obtained by conventional plate count method.

Example 3

[Determination of Template DNA by PCR Method Employing a Microplate]

In each of the wells of a microplate as used in Example 2, 1 μl of 2.4-bis(4-N,N-dimethylaminophenyl)-6-methylpyrylium iodide solution in acetonitrile and the primers (two kinds of primers, 10 pmoles) as used in Example 2 were applied and dried.

Separately, from 2 ml of an overnight culture of $E.\ coli$, DNA of $E.\ coli$ was extracted in the same manner as in Example 2, and the extract was diluted 100-fold to obtain a template DNA solution.

This template DNA solution was serially diluted in the same manner as in Example 2. The dilutions were added by 1 μl each to the wells of the microplate as shown in FIG. 5. To each of the wells, the PCR reaction solution was added which contains one Ampli Wax PCR Gem 100 (made by Perkin-Elmer) and the components below:

| | |
|---|---|
| 10× buffer: | 5 μl |
| dNTPs: | 5 μl |
| Taq DNA Polymerase: | 0.5 unit |

Further, to each of the wells, sterilized water was added to the total volume of 50 μl. Then PCR was carried out with a PCR apparatus, Model PTC-100-96 (made by MJ Research Inc.), under the same conditions as in Example 1.

Figure 7:
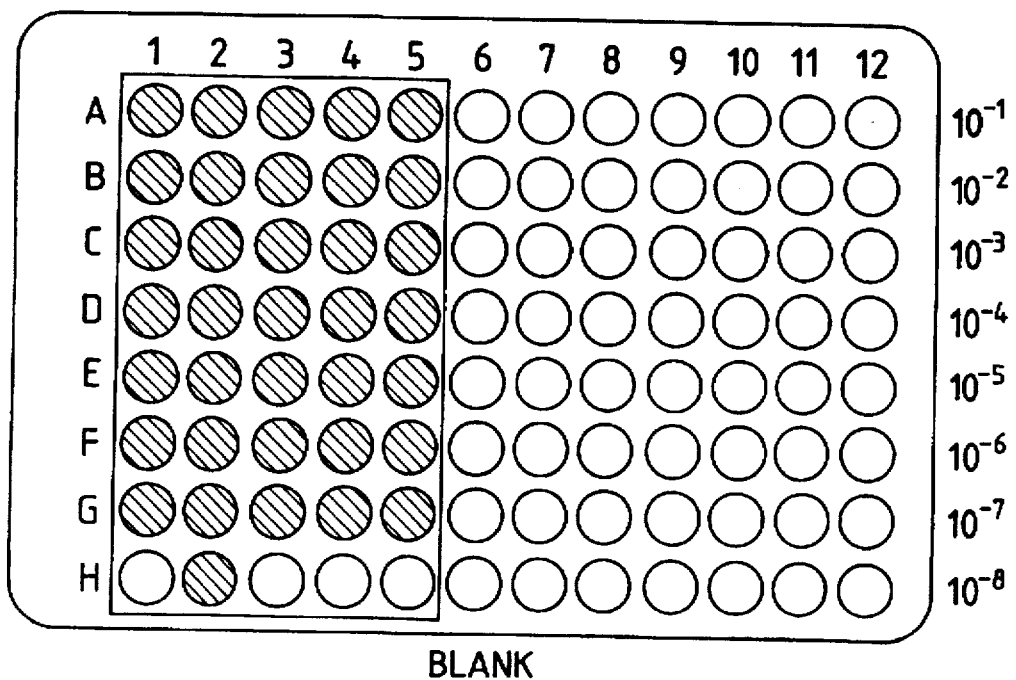
FIG. 7 shows the position of the wells of which fluorescence intensity were twice or more that of the blank value in Example 3.

After the PCR reaction, 5 μl of acetonitrile was added to each of the wells on the microplate. Each of the mixture was agitated sufficiently, and was left standing for 5 minutes. Then the microplate was set on a Millipore Fluorescence Apparatus (CytoFluor 2350), and the fluorescence was measured with the same filters employed in Example 1. FIG. 7 shows the results. The wells producing fluorescence of twice or more that of the blank wells were regarded to contain the PCR amplification product (shadowed wells in FIG. 5). From the results, the number of the template DNA molecules was estimated to be $3.5 \times 10^7$ by reference to the table for MPN. In consideration of the initial dilution by the factor of 100, the number of the template DNA molecules was estimated to be $3.5 \times 10^9$.

Comparative Example 4

The number of the bacterial cells in the 2 ml of $E.\ coli$ culture used in Example 3 was determined by plate count method. Consequently, the number was found to be $4 \times 10^9$, which agrees approximately with the results obtained in Example 3.

The desirable dilution degree of a DNA template and the desirable concentration range thereof for MPN detection can be decided, and the sample concentration can be set according to the results of Examples 2 and 3. Therefore calibration curves can be prepared for the number of the cells, the copy number, and the amount of template DNA.

Example 4

[Detection Kit for Cancer-Specific Gene by PCR]

(1) Extraction of mRNA:

Two tissue samples of 5 mm cube were taken out respectively from two cancer-suspected sites of the large intestine of a patient by biopsy. The samples are hereinafter referred to as "Tissue A" and "Tissue B". From the tissue samples, mRNA was extracted by a conventional manner as follows (by reference to "Shin Seikagaku Jikken Koza (New Library of Experiments in Biochemistry)" vol. 2, Nucleic acid I, page 48): 2 ml of D Solution (4M guanidine thiocyanate, 25 mM sodium citrate (pH 7.0), 0.5% sodium N-lauroylsarcosinate, and 0.1M 2-mercaptoethanol) was added to each of the tissue samples, and the tissue was immediately homogenized in a sterilized tube by means of Polytron three times each for 10 seconds. Thereto were added successively 0.2 ml of 2M sodium acetate (pH 4), 2 ml of water-saturated phenol, and 0.4 ml of chloroform-isopentyl alcohol (49:1 in volume ratio) with sufficient stirring at each addition. The mixture was shaken by means of a Vortex mixer for 10 seconds, cooled with ice for 15 minutes, and subjected to centrifugation at 4° C. at 10000×g for 20 minutes. After the centrifugation, to the aqueous layer, an equal amount of isopropyl alcohol was added, and the mixture was left standing at −20° C. overnight. The mixture was then centrifuged as above and 0.6 ml of D Solution was added to dissolve the precipitate. Thereto an equal amount of isopropyl alcohol was added. The mixture was cooled at −20° C. for one hour, and centrifuged at 4° C. at 10000×g for 20 minutes. The obtained precipitate was suspended in 75% ethanol, and the suspension was centrifuged again at 10000× g, at 4° C. for 20 minutes. The precipitate was dried as a crude RNA fraction, which was heated at 65° C. for 5 minutes, then cooled rapidly to room temperature, and was washed with an equal amount of a 2× TNEL buffer solution [20 mM Tris-hydrochloric acid buffer solution (pH 7.6), 0.5M sodium chloride, 1 mM EDTA, and 0.1% sodium N-lauroylsarcosinate]. The washed crude RNA fraction was applied to an oligo(dT)-cellulose column made by Pharmacia) equilibrated with a TNEL buffer solution, and mRNA was eluted with an extraction solution (TNEL buffer solution without 0.5M sodium chloride).

(2) Preparation of cDNA:

Double-stranded cDNA was prepared from the above mRNA by means of TimeSaver™ cDNA Synthesis Kit.

(3) Constitution of quantitative determination kit:

The primers used for detection of large intestine cancer have following nucleotide sequences.

Primer 1: 5' GACTCTGGAGTGAGAATCATA 3' (Sequence No. 5)

Primer 2: 5' ATCCAATCACCCACATGCATT 3' (Sequence No. 6)

To the bottom of Vessel 1 (an Epfendorf tube) as shown in FIGS. 9A to 9C, Primer 1 and Primer 2 were applied to an amount of 10 pmoles respectively. In the container 2 prepared from paraffin-coated paper, the components below were packed.

| | |
|---|---|
| dNTPs: | 5 μl |
| Taq polymerase: | 0.5 unit |
| 150 μg/ml 2,4-bis(4-N,N-dimethylaminophenyl)-6-methylpyrylium iodide solution in acetonitrile: | 1 μl |
| 10× buffer: | 5 μl |
| Distilled water: (freeze stored) | 39 μl |

The container 2 was set in the vessel 1 as shown in FIG. 9B to make up a kit. The cDNA samples obtained above from each of the aforementioned Tissue A and Tissue B were serially diluted, 1-fold (no dilution), 2-fold, 10-fold, 50-fold, 100-fold, 1000-fold, and 10000-fold. Each dilution (including non-diluted sample) was injected with a Pipetman to the bottom of vessel 1 of the kit, breaking through the paraffin-coated paper container 2. After the injection of cDNA, the vessels were centrifuged to transfer the contents of the container 2 completely to the reaction zone 5 containing the primers. After confirming the complete transfer, the broken empty containers 2 were taken out from the vessel 1. Thereto, one Ampli Wax, PCR Gen 100 (made by Perkin-Elmer Co.) was added.

Figure 8:
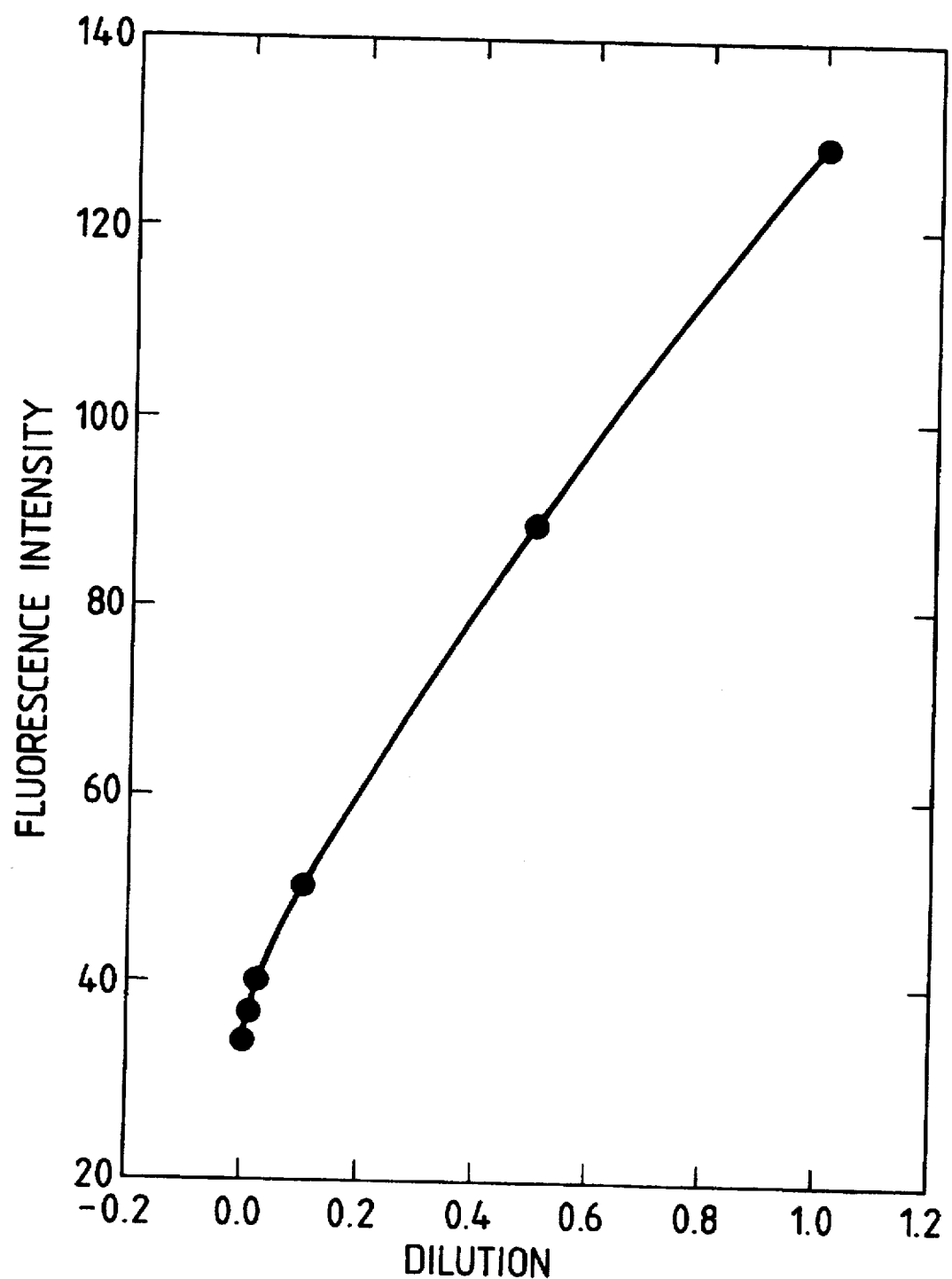
FIG. 8 shows the results of Example 4 with the sample from the tissue A.

(4) Practice of PCR, and detection:

PCR was conducted in the same manner as in Example 1. The samples in the vessels were subjected to fluorescence measurement without further dilution. The results regarding Tissue A are shown in FIG. 8. The target gene amplification was observed with Tissue A, and the amplification product was formed quantitatively corresponding to the dilution degree of the template DNA. On the contrary, no fluorescence was observed with Tissue B.

(5) Examination by electrophoresis:

After the detection, DNA was recovered from the samples by precipitation with ethanol. The recovered matter was examined by agarose gel electrophoresis. The DNA from Tissue A gave a band at 317 bp at the 1-fold (not diluted) to 1000-fold dilutions, whereas no band was observed with Tissue A at 10000-fold dilution, the blank samples containing primers only, and the samples derived from Tissue B.

Comparative Example 5

The above Tissue A and Tissue B were examined by a conventional culture method. Tissue A exhibited multiplication, and was diagnosed as a malignant cancer, whereas Tissue B did not exhibit multiplication, and was diagnosed as benign polyp.

According to the present invention, the dye compounds which react selectively with double-stranded nucleic acid are used for detection of the PCR amplification products, enabling simplification of detection, quantitative determination, and measurement of the number of the cells with precision.

What is claimed is:

1. A method for quantifying a target nucleic acid, comprising the steps of:

conducting PCR of a nucleic acid sample with a primer set required for amplification of a specific base sequence region of the target nucleic acid to provide a double stranded nucleic acid;

reacting the double-stranded nucleic acid with a dye compound represented by the following formula to bind the dye compound to the double stranded nucleic acid; and measuring intensity of the fluorescence from the dye compound bound to the double-stranded nucleic acid to quantitatively determine the target nucleic acid in the sample,

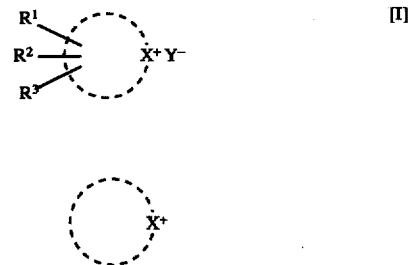

wherein is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

R³ is a group of —A or —L—A wherein L is —L¹—, —L²—L³—, or —L⁴—L⁵—L⁶—, L¹ to L⁶ being independently —(CH=CH)—, a bivalent group derived from a substituted or unsubstituted aryl group, a substituted or unsubstituted alkylene group, or —CH=R⁴—, wherein R⁴ is a cyclic structure having an oxo group; A is a substituted or unsubstituted aryl group, or —CH=R⁵, wherein R⁵ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to R¹, R², or R³ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and Y⁻ is an anion.

2. The method according to claim 1, wherein the dye compound bound to the double-stranded nucleic acid is inserted into a double helix structure of the double-stranded nucleic acid as an intercalator.

3. The method according to claim 1, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

4. The method according to claim 1, wherein the dye compound is insoluble in water; PCR is conducted in an aqueous reaction system containing the dye compound and an aqueous medium; and a solvent is added to the reaction system after the PCR to dissolve the dye compound thus enabling the reaction with the double-stranded nucleic acid resulting from the PCR.

5. The method according to claim 1, wherein the double-stranded nucleic acid has a chain length of not less than 100 base pairs.

6. The method according to claim 1, wherein each primer in said primer set has a chain length of 30 bases or less.

7. A kit for quantifying a target nucleic acid in a sample, comprising:

a reactor containing a reaction chamber for PCR, in which a required amount of a dye compound represented by the following formula is provided,

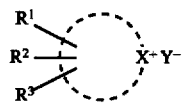

[I]

wherein

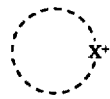

is (i) a pyrylium ring or (ii) a pyrylium-analog ring of 5 or 6 members where X is O, S, Se, or Te; R¹ and R² are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl group;

R³ is a group of —A or —L—A wherein L is L—L¹—, —L²—L³—, or —L⁴—L⁵—L⁶—, L¹ to L⁶ being independently —(CH=CH )—, a bivalent group derived from a substituted or unsubstituted aryl group, a substituted or unsubstituted alkylene group, or —CH=R⁴—, wherein R⁴ is a cyclic structure having an oxo group; A is a substituted or unsubstituted aryl group, or —CH=R⁵, wherein R⁵ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to R¹, R², or R³ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and Y⁻ is an anion.

8. The kit according to claim 7, wherein the reactor further contains in the reaction chamber a required amount of a primer set which is necessary for the PCR amplification of a specific sequence region of a target nucleic acid.

9. The kit according to claim 7, wherein the dye compound represented by the general formula is a 2,4-bis(4-N, N-dimethylaminophenyl)-6-methylpyrylium salt, or a 2,4-bis(4-N,N-dimethylaminophenyl)-6-methylthiopyrylium salt.

10. The kit according to claim 7, wherein the dye compound is water-insoluble, and a solvent is provided to dissolve the dye compound thus enabling reaction of the dye compound with a double-stranded nucleic acid resulting from the PCR in the reaction chamber.

11. A kit for quantifying a target nucleic acid, comprising:

a reaction chamber for PCR; and a reagent chamber, wherein the reagent chamber contains a dye compound represented by the following formula, and the reagent chamber is provided so that the dye compound in the reagent chamber is transferred to the reaction chamber,

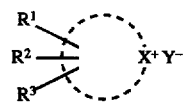

[I]

wherein

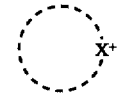

is (i) a pyrylium ring or (ii) a pyrylium-analog ring of 5 or 6 members where X is O, S, Se, or Te; R¹ and R² are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, —$L^2$—$L^3$—, or —$L^4$—$L^5$—$L^6$—, $L^1$ to $L^6$ being independently —(CH=CH)—, a bivalent group derived from a substituted or unsubstituted lower alkyl group, a substituted or unsubstituted aryl group, a substitute or unsubstituted lower aralkyl group, or a substituted or unsubstituted cycloalkyl group;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted lower aralkyl group; and $Y^-$ is an anion.

12. The kit according to claim 11, wherein a reagent for the PCR is further contained in the reagent chamber.

13. A kit according to claim 11, wherein the reagent chamber comprises a plurality of sub-chambers, one of which contains the dye compound, and another sub-chamber contains a reagent for PCR.

14. The kit according to claim 11, wherein a necessary amount of a primer set required for PCR amplification of a specific sequence region of target nucleic acid is contained in the reaction chamber.

15. The kit according to claim 11, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

16. The kit according to claim 11, wherein the dye compound is water-insoluble, and a solvent is provided to dissolved the dye compound, thus enabling the reaction of the dye compound with a double-stranded nucleic acid resulting from the PCR in the reaction chamber.

17. The kit according to claim 11, wherein a solution of the dye compound is placed in the reagent chamber.

18. A method for measuring a number of a target microorganism or target cells, a number of a specific gene, or a copy number of a specific gene, comprising the steps of:
extracting nucleic acid from a sample containing a microorganism or cells to be detected;
providing a serial dilution of the extracted nucleic acid;
conducting PCR with respect to each of the sample dilutions containing extracted nucleic acid with a primer set required for amplificatin of a specific base sequence region of the extracted nucleic acid to provide double-stranded nucleic acid;
reacting the resulting double-stranded nucleic acid with a dye compound represented by the following formula to bind the dye compound to the double-stranded nucleic acid; and
measuring intensity of the fluorescence from the dye compound inserted into the double-stranded nucleic acid; and deriving the number of the microorganism or cells,-the specified genes, or copies of the specified genes in the sample on the basis of the dilution rate at which fluorescence is observed,

wherein

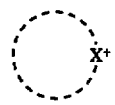

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—$L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

19. The method according to claim 18, wherein the dye compound bound to the double-stranded nucleic acid is inserted into a double helix structure of the double-stranded nucleic acid as an intercalator.

20. The method according to claim 18, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

21. The method according to claim 18, wherein the dye compound is water-insoluble, and the PCR is conducted in a reaction system containing the water-insoluble dye compound and an aqueous medium, a solvent is added after the PCR to the reaction system to dissolve the dye compound thus enabling the reaction of the dye compound with the double-stranded nucleic acid resulting from the PCR.

22. The method according to claim 18, wherein the double-stranded nucleic acid has a chain length of not less than 100 base pairs.

23. The method according to claim 18, wherein each primer in said primer set has a chain length of 30 bases or less.

24. A kit for measuring a number of a target microorganism or target cells, a number of a specific gene, or a copy number of the specific gene, comprising:

a reactor comprising a plurality of reaction chambers for serially diluting a nucleic acid extracted from a sample containing microorganisms or cells to be detected, each of the reaction chambers containing a dye compound represented by the following formula, wherein the reaction chambers are employed for the PCR to amplify a specific sequence of the extracted nucleic acid which is peculiar to the microorganisms or cells,

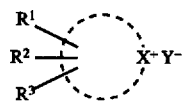     [I]

wherein

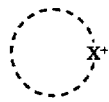

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

25. The kit according to claim 24, wherein the dye compound represented by the general formula is a 2,4-bis(4-N,N-dimethylaminophenyl)-6-methylpyrylium salt, or a 2,4-bis(4-N,N-dimethylaminophenyl)-6-methylthiopyrylium salt.

26. The kit according to claim 24, wherein the dye compound is water-insoluble, and a solvent is provided for dissolving the dye compound thus enabling the reaction of the dye compound with a double-stranded nucleic acid resulting from the PCR in the reaction chamber.

27. The kit according to claim 24, wherein the reaction chamber further contains a primer set for PCR amplification of a sequence characteristic of the microorganism or cells to be detected.

28. A method for quantifying a target nucleic acid in a sample, comprising the steps of:

subjecting a sample containing a nucleic acid to be detected to MPN-PCR with a primer set required for amplification of a specific base sequence region of the target nucleic acid to provide a double-stranded nucleic acid;

reacting the double-stranded nucleic acid with a dye compound represented by the following formula to bind the dye compound to the double-stranded nucleic acid; and measuring intensity of the fluorescence of the dye compound inserted into the double-stranded nucleic acid to quantify the target nucleic acid in the sample,

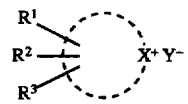     [I]

wherein

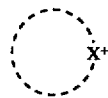

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group); A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

29. The method according to claim 28, wherein the dye compound bound to the double-stranded nucleic acid is inserted into a double helix structure of the double-stranded nucleic acid as an intercalator.

30. The method according to claim 28, wherein the dye compound represented by the general formula is a 2,4-bis(4-N,N-dimethylaminophenyl)-6-methylpyrylium salt, or a 2,4-bis(4-N,N-dimethylaminophenyl)-6-methylthiopyrylium salt.

31. The method according to claim 28, wherein the dye compound is insoluble in water; the MPN-PCR is conducted in an aqueous reaction system containing the dye compound and an aqueous medium; and a solvent is added to the reaction system after the MPM-PCR to dissolve the dye compound thus enabling the reaction of the dye compound with the double-stranded nucleic acid resulting from the MPN-PCR.

32. The method according to claim 28, wherein the double-stranded nucleic acid has a chain length of not less than 100 base pairs.

33. The method according to claim 28, wherein each primer in said primer set has a chain length of 30 bases or less.

34. A kit for quantifying a target nucleic acid in a sample, comprising:

a reactor comprising reaction chambers for MPN-PCR, wherein in each of the reaction chambers a required amount of a dye compound represented by the following formula is contained,

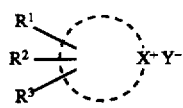 [I]

wherein

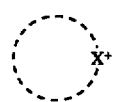

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, —$L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or substituted lower alkyl group, a substituted or unsubstituted aryl group, or a substituted or unsubstituted lower aralkyl group; and $Y^-$ is an anion.

35. The kit according to claim 34, wherein the reactor further contains in the reaction chamber a required amount of a primer set which is necessary for MPN-PCR amplification of a specific sequence region of target nucleic acid.

36. The kit according to claim 34, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

37. A kit for quantifying a target nucleic acid in a sample comprising a reaction chamber for MPN-PCR and a reagent chamber, wherein the reagent chamber contains a required amount of a dye compound represented by the following formula, and the reagent chamber is provided so that the dye compound in the reagent chamber is transferred to the reaction chamber,

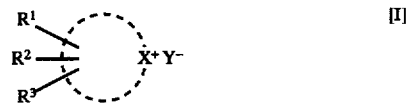 [I]

wherein

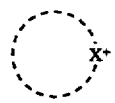

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, —$L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

38. The kit according to claim 37, wherein a reagent for MPN-PCR is further contained in the reagent chamber.

39. The kit according to claim 37, wherein the reagent chamber comprises a plurality of sub-chambers, one of which contains the dye compound, and another sub-chamber contains a reagent for MPN-PCR.

40. The kit according to claim 37, wherein a necessary amount of a primer set required for MPN-PCR amplification of a specific sequence region of a target nucleic acid is contained further in the reaction chamber.

41. The kit according to claim 37, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

42. The kit according to claim 37, wherein the dye compound is water-insoluble, and a solvent is provided to dissolve the dye compound thus enabling the reaction of the dye compound with a double-stranded nucleic acid resulting from the MPN-PCR in the reaction chamber after the MPN-PCR.

43. The kit according to claim 37, wherein a solution of the dye compound is placed in the reagent chamber.

44. A method for measuring a number of a target microorganism or target cells, a number of a specific gene, or a copy number of a specific gene, comprising the steps of:

extracting nucleic acid from a sample containing a microorganism or cells to be detected;

providing a serial dilution of the extracted nucleic acid;

conducting MPN-PCR with respect to each of the diluted samples containing extracted nucleic acid with a primer set required for amplification of a specific base sequence region of the extracted nucleic acid to provide a double-stranded nucleic acid;

reacting the double-stranded nucleic acid with a dye compound represented by the following formula to bind the dye compound to the double-stranded nucleic acid;

measuring intensity of the fluorescence from the dye compound inserted into the double-stranded nucleic acid; and deriving the number of the microorganisms or cells, the specified genes, or copies of the specified genes in the sample on the basis of the dilution rate at which fluorescence is still observed,

   [I]

wherein

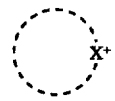

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=$R^4$—, wherein $R^4$ is a cyclic structure having an oxo group; A is a substituted or unsubstituted aryl group, or —CH=$R^5$, wherein $R^5$ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

45. The method according to claim 44, wherein the dye compound bound to the double-stranded nucleic acid is inserted into a double helix structure of the double-stranded nucleic acid as an intercalator.

46. The method according to claim 44, wherein the dye compound represented by the general formula is a 2,4-bis (4-N,N-dimethylaminophenyl)-6-methylpyrylium salt, or a 2,4-bis(4-N,N-dimethylaminophenyl)-6-methylthiopyrylium salt.

47. The method according to claim 44, wherein the dye compound is water-insoluble, and PCR is conducted in a reaction system containing the water-insoluble dye compound and an aqueous medium, a solvent is added after the MPN-PCR to the reaction system to dissolve the dye compound thus enabling reaction of the dye compound with the double-stranded nucleic acid resulting from the MPN-PCR.

48. The method according to claim 44, wherein the double-stranded nucleic acid has a chain length of not less than 100 base pairs.

49. The method according to claim 44, wherein each primer in said primer set has a chain length of 30 bases or less.

50. A kit for measuring a number of a target microorganism or target cells, a number of a specific genes, or a copy number of the specific gene, comprising a reactor comprising a plurality of reaction chambers for serially diluting a nucleic acid extracted from a sample containing a microorganism or cells to be detected, each of the reaction chambers containing a dye compound represented by the following formula, wherein the reaction chambers are employed for the MPN-PCR to amplify a specific sequence of the extracted nucleic acid which is peculiar to the microorganisms of cells,

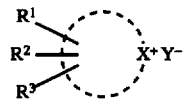   [I]

wherein

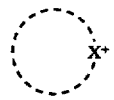

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=R⁴—, wherein R⁴ is a cyclic structure having an oxo group; A is a substituted or unsubstituted aryl group, or —CH=R⁵, wherein R⁵ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and Y⁻ is an anion.

51. The kit according to claim 50, wherein the dye compound represented by the general formula is a 2,4-bis(4-N,N-dimethylaminophenyl)-6-methylpyrylium salt, or a 2,4-bis(4-N,N-dimethylaminophenyl)-6-methylthiopyrylium salt.

52. The kit according to claim 51, wherein the dye compound is water-insoluble, and a solvent is provided for dissolving the dye compound thus enabling reaction of the dye compound with a double-stranded nucleic acid resulting from the MPN-PCR in the reaction chamber.

53. The kit according to claim 50, wherein the reaction chamber further contains a primer set for PCR amplification of a sequence characteristic of the microorganism or cells to be detected.

54. A method for quantifying a target nucleic acid, comprising the steps of:

conducting PCR of a nucleic acid sample with a primer set required for amplification of a specific base sequence region of the target nucleic acid to provide a double-stranded nucleic acid in the presence of a dye compound represented by the following formula; and measuring intensity of the fluorescence from the dye compound to quantitatively determine the target nucleic acid in the sample,

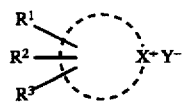 [I]

wherein

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=R⁴—, wherein R⁴ is a cyclic structure having an oxo group; A is a substituted or unsubstituted aryl group, or —CH=R⁵ wherein R⁵ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and Y⁻ is an anion.

55. The method according to claim 54, wherein the fluorescence-emitting dye compound is inserted into a double helix structure of the double-stranded nucleic acid to bind the double-stranded nucleic acid.

56. A method for quantifying a target nucleic acid, comprising the steps of:

conducting PCR of a nucleic acid sample with a primer set required for amplification of a specific base sequence region of the target nucleic acid to provide a PCR amplified product containing a double-stranded nucleic acid;

adding a dye compound represented by the following formula to the PCR-amplified product; and measuring intensity of the fluorescence from the dye compound in the PCR-amplified product to quantitatively determine the target nucleic acid in the sample,

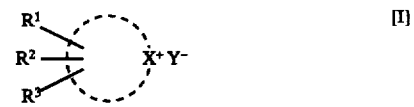 [I]

wherein

is (i) a pyrylium ring or (ii) a pyrylium-analog ring of 5 or 6 members where X is O, S, Se, or Te; $R^1$ and $R^2$ are independently a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower aralkyl group, or a substituted or unsubstituted cycloalkyl;

$R^3$ is a group of —A or —L—A wherein L is —$L^1$—, $L^2$—$L^3$—, or —$L^4$—$L^5$—$L^6$—, $L^1$ to $L^6$ being independently —(CH=CH)—, a bivalent group derived from a substituted or unsubstituted aryl group, a substituted or unsubstituted alkylene group, or —CH=R⁴—, wherein R⁴ is a cyclic structure having an oxo group; A is a substituted or unsubstituted aryl group, or —CH=R⁵, wherein R⁵ is a substituted or unsubstituted heterocycle, a substituted or unsubstituted cycloalkyl group, or a substituted or unsubstituted aromatic ring;

in the pyrylium ring or a pyrylium-analogous ring containing X, the hydrogen atom bonded to the carbon atom which is not linked to $R^1$, $R^2$, or $R^3$ may be substituted by a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, or a substituted or unsubstituted lower aralkyl group; and $Y^-$ is an anion.

57. The method according to claim 56, wherein the fluorescence-emitting dye compound is inserted into a double helix structure of the double-stranded nucleic acid in the PCR-amplified product.

58. The kit according to claim 34, wherein the dye compound is water-insoluble, and a solvent is provided for dissolving the dye compound thus enabling the reaction of the dye compound with a double-stranded nucleic acid resulting from the PCR in the reaction chamber.

59. The method according to claim 57, wherein the fluorescence-emitting dye compound is inserted into a double helix structure of the double-stranded nucleic acid in the PCR-amplified product as an intercalator.

* * * * *

UNITED STATES PATENT AND TRADEMARK OFFICE
CERTIFICATE OF CORRECTION

PATENT NO. : 5,670,315

DATED : September 23, 1998

INVENTOR(S) : NOBUKO YAMAMOTO, ET AL.

Page 1 of 5

It is certified that error appears in the above-identified patent and that said Letters Patent is hereby corrected as shown below:

ON THE TITLE PAGE:

AT [56] REFERENCES CITED - OTHER PUBLICATIONS

After "Detty": "chacogenapyrlium" should read --chalogenapyrylium--.

COLUMN 2

Line 52, "$10^n$" should read --$10^{-n}$--.

COLUMN 7

Line 22, "form" should read --form a--.

UNITED STATES PATENT AND TRADEMARK OFFICE
CERTIFICATE OF CORRECTION

PATENT NO. : 5,670,315
DATED : September 23, 1998
INVENTOR(S) : NOBUKO YAMAMOTO, ET AL.

It is certified that error appears in the above-identified patent and that said Letters Patent is hereby corrected as shown below:

COLUMN 31

Line 30, " " should read -- -- .

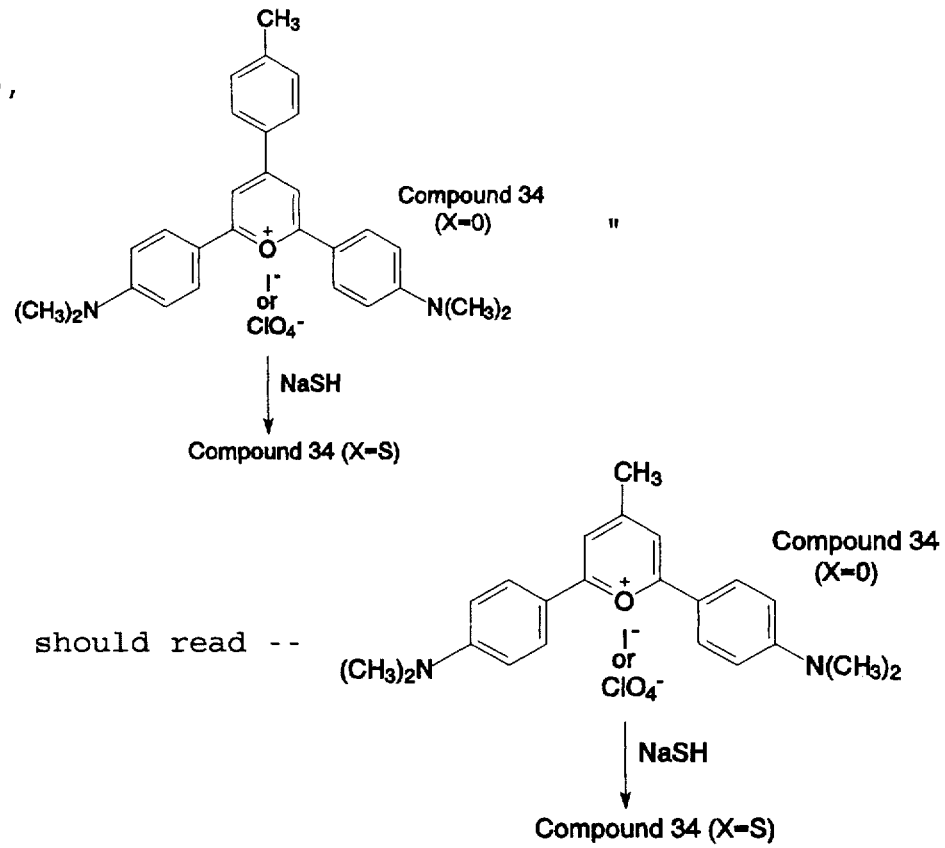

COLUMN 42

Line 51, "sM." should read --$^5$M.--; and
Line 54, "SiGma" should read --Sigma--.

UNITED STATES PATENT AND TRADEMARK OFFICE
CERTIFICATE OF CORRECTION

PATENT NO. : 5,670,315

DATED : September 23, 1998

INVENTOR(S) : NOBUKO YAMAMOTO, ET AL.   Page 3 of 5

It is certified that error appears in the above-identified patent and that said Letters Patent is hereby corrected as shown below:

COLUMN 46

Line 26, "107, about 106, about 105, and about 104" should read -- $10^7$, about $10^6$, about $10^5$, and about $10^4$ --.

COLUMN 48

Line 56, "column" should read --column (--.

COLUMN 53

Line 5, "$L^2$-$L^3$-," should read -- -$L^2$-$L^3$-, --.

COLUMN 54

Line 5, "L-$L^1$-," should read -- -$L^1$-, --.

COLUMN 55

Line 8, "$L^2$-$L^3$-" should read -- -$L^2$-$L^3$-, --; and
Line 57, "amplificatin" should read --amplification--.

COLUMN 56

Line 1, "-the" should read --the--;
Line 18, "$\phi$," (zero) should read --O,--;
Line 26, "-$L^{1,}$" should read -- -$L^1$-, --; and
Line 27, "$L^2$-$L^3$-," should read -- -$L^2$-$L^3$-, -- and
"-$L^4$-$L^5$-$L^6$-$L^1$" should read -- -$L^4$-$L^5$-$L^6$, $L^1$ --.

UNITED STATES PATENT AND TRADEMARK OFFICE
CERTIFICATE OF CORRECTION

PATENT NO. : 5,670,315

DATED : September 23, 1998

INVENTOR(S) : NOBUKO YAMAMOTO, ET AL.    Page 4 of 5

It is certified that error appears in the above-identified patent and that said Letters Patent is hereby corrected as shown below:

COLUMN 57

Line 33, "$L^2-L^3,$" should read -- $-L^2-L^3-,$ --.

COLUMN 58

Line 36, "$L^2-L^3-,$" should read -- $-L^2-L^3-,$ --; and
Line 41, "group);" should read --group;--.

COLUMN 59

Line 3, "MPM-PCR" should read --MPN-PCR--; and
Line 57, "substituted" (first occurrence) should read --unsubstituted--.

COLUMN 60

Line 5, "comprising" should read --comprising:--.

COLUMN 61

Line 30, "microorganisms" should read --microorganism--;
Line 56, "$L^2-L^3-,$" should read -- $-L^2-L^3-,$ --; and
Line 60, "$-CH=R^4,$" should read -- $-CH=R^4-,$ --.

UNITED STATES PATENT AND TRADEMARK OFFICE
CERTIFICATE OF CORRECTION

PATENT NO. : 5,670,315
DATED : September 23, 1998
INVENTOR(S) : NOBUKO YAMAMOTO, ET AL.

It is certified that error appears in the above-identified patent and that said Letters Patent is hereby corrected as shown below:

COLUMN 62

Line 32, "genes," should read --gene,--;
Line 33, "comprising" should read --comprising:--;
Line 41, "microorganisms of cells" should read --microorganism or cells--; and
Line 65, "$L^2-L^3-,$" should read -- $-L^2-L^3-,$ --.

COLUMN 63

Line 65, "$L^2-L^3-,$" should read -- $-L^2-L^3-,$ --.

COLUMN 64

Line 55, "$L^2-L^3-,$" should read -- $-L^2-L^3-,$ --.

Signed and Sealed this

Fifth Day of May, 1998

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGAGTTTGAT CATGGCTCAG                                                  2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AACCCAACAT CTCACGACAC                                                  2 0

( 2 ) INFORMATION FOR SEQ ID NO:3:

```
( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

AGAGTTTGAT CCTGGCTCAG                                           20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AACCCAACAT CTCACGACAC                                           20

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GACTCTGGAG TGAGAATCAT A                                         21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ATCCAATCAC CCACATGCAT T                                         21
```